US011925793B2

(12) United States Patent
Moser

(10) Patent No.: US 11,925,793 B2
(45) Date of Patent: Mar. 12, 2024

(54) APPARATUS FOR INJECTING A FLUID, COMPRISING A NEEDLE ASSEMBLY AND A NEEDLE RETENTION DEVICE FOR RETAINING A NEEDLE OF THE NEEDLE ASSEMBLY WHEN ATTACHED TO THE APPARATUS, AND NEEDLE RETENTION DEVICE

(71) Applicant: SCHOTT Pharma Schweiz AG, St. Gallen (CH)

(72) Inventor: Raymond Moser, Engelburg (CH)

(73) Assignee: SCHOTT Pharma Schweiz AG, St. Gallen (CH)

( * ) Notice: Subject to any disclaimer, the term of this patent is extended or adjusted under 35 U.S.C. 154(b) by 550 days.

(21) Appl. No.: 16/993,555

(22) Filed: Aug. 14, 2020

(65) Prior Publication Data
US 2021/0046255 A1     Feb. 18, 2021

(30) Foreign Application Priority Data
Aug. 15, 2019     (EP) ..................................... 19191947

(51) Int. Cl.
*A61M 5/34*     (2006.01)
(52) U.S. Cl.
CPC ..... *A61M 5/347* (2013.01); *A61M 2205/6081* (2013.01)
(58) Field of Classification Search
CPC .......... A61M 5/347; A61M 2205/6081; A61M 5/346
See application file for complete search history.

(56) References Cited

U.S. PATENT DOCUMENTS

| 1,524,242 | A | 1/1925 | Hein |
| 1,668,315 | A | 5/1928 | Hein |
| 2,047,512 | A | 7/1936 | Kauffman |
| 2,806,473 | A | 9/1957 | Lingley |

(Continued)

FOREIGN PATENT DOCUMENTS

| DE | 10 2013 210 998 A1 | 12/2014 |
| EP | 0 980 276 B1 | 10/2002 |

(Continued)

OTHER PUBLICATIONS

European Office Action dated Nov. 5, 2019 for European Application No. 19191947.1 (7 pages).

*Primary Examiner* — Bradley J Osinski
(74) *Attorney, Agent, or Firm* — Taylor IP, P.C.

(57) ABSTRACT

An apparatus for injecting a fluid includes: an injector including a cylindrical container, a coupling portion, and a peripheral section; a needle assembly including a needle and a hub defining a contact area, the coupling portion configured to be coupled with the hub; and a needle retention device including a needle-retainer portion having a finger configured to radially extend over at least a part of the contact area of the hub, a container-contact portion defining a first opening configured to be attached in a form-fitting way onto the peripheral section of the container. When the apparatus is in its operational state, the hub of the needle assembly is coupled to the coupling portion, the container-contact portion is attached to the container, and the finger of the needle-retainer portion extends over the contact area of the hub when the needle retention device is in its retaining position.

20 Claims, 12 Drawing Sheets

(56) References Cited

U.S. PATENT DOCUMENTS

| | | | |
|---|---|---|---|
| 4,490,142 A | | 12/1984 | Silvern |
| 4,822,343 A | | 4/1989 | Beiser |
| 5,466,223 A | * | 11/1995 | Bressler .............. A61M 5/3269 |
| | | | 604/110 |
| 5,759,178 A | | 6/1998 | Wells |
| 5,925,032 A | | 7/1999 | Clements |
| 6,716,192 B1 | * | 4/2004 | Orosz, Jr. .......... A61B 5/15003 |
| | | | 604/117 |
| 2009/0177158 A1 | * | 7/2009 | Krumme ........... A61M 5/14526 |
| | | | 604/143 |
| 2010/0016829 A1 | * | 1/2010 | Krumme ............... A61M 5/344 |
| | | | 604/506 |
| 2010/0167829 A1 | | 7/2010 | Rhodes |

FOREIGN PATENT DOCUMENTS

| | | |
|---|---|---|
| EP | 1 521 608 B1 | 12/2010 |
| EP | 1 971 382 B1 | 9/2016 |
| EP | 3 187 218 A1 | 7/2017 |
| FR | 574431 | 7/1924 |
| WO | 90/11789 | 10/1990 |
| WO | 2005/065753 A1 | 7/2005 |
| WO | 2013/004675 A1 | 1/2013 |
| WO | 2015/167150 A2 | 11/2015 |

\* cited by examiner

APPARATUS FOR INJECTING A FLUID, COMPRISING A NEEDLE ASSEMBLY AND A NEEDLE RETENTION DEVICE FOR RETAINING A NEEDLE OF THE NEEDLE ASSEMBLY WHEN ATTACHED TO THE APPARATUS, AND NEEDLE RETENTION DEVICE

CROSS REFERENCE TO RELATED APPLICATIONS

The present application claims priority to European Patent Application EP 19191947.1, filed Aug. 15, 2019, which is incorporated in its entirety herein by reference.

BACKGROUND OF THE INVENTION

1. Field of the Invention

The present invention relates to an apparatus for injecting a fluid, including an injector for injecting a fluid, such as a syringe for injecting a medical, diagnostic, cosmetic or dental preparation, for example, a needle assembly, including a needle and a hub for mounting the needle to the injector, and devices and methods to be attached to the apparatus.

2. Description of the Related Art

Application devices such as apparatuses for injecting a fluid, including an injector for injecting a fluid, e.g. a syringe, are well known. Typically, such injectors may include a fluid that may be stored in a cavity or a container thereof. The fluid may be a liquid or semi-liquid material, for example a medical, diagnostic, cosmetic or dental preparation, to be injected into a patient's body.

When the apparatus is in its operational state for injecting a fluid stored in the container, a cannula or needle is normally connected to the injector, may be coupled to a coupling portion at the distal end or mouth of the injector. For injecting the fluid stored in the container, a compression force is then applied to the fluid in order to discharge the fluid out of the container and through the inner channel of the needle.

For special applications, the fluid may be pasty or highly viscous, e.g. when injecting specific cosmetic preparations. In such a case, the compression force necessary for discharging the pasty fluid may become quickly very high. This may lead to the risk of a detachment of the needle assembly and/or the needle from the injector when injecting the fluid, if the pressure to the fluid is too high. This may be much worse when such a needle detachment takes place during an injection of the fluid.

From WO 2013/004675 A1 is known an accessory for a syringe for holding a needle on the syringe in order to avoid a risk of detachment during injection of a fluid. The needle is attached to the syringe via a so-called Luer lock connection to the distal end of the syringe, wherein a Luer lock hub of the needle assembly can be retained by the accessory. The accessory includes a bearing element that is designed and arranged such that a force exerted by the user on the accessory and which is essentially oriented parallel to the longitudinal axis of the syringe results in a force applied by the accessory on the needle which includes a longitudinal component oriented parallel to the longitudinal axis of the syringe and a radial oriented component perpendicular to this axis and towards the center of the syringe. Thus, this accessory works together with the Luer lock portion of the needle only.

From EP 0 980 276 B1 is known a cannula holder for a syringe, wherein this cannula holder includes a sleeve having a bore for receiving a complete syringe. The assembly of the syringe and the cannula holder is sophisticated.

From WO 2015/167150 A2 is known a syringe holder for preventing separation of the syringe needle, the syringe body comprising a syringe mounting space for accommodation a complete syringe.

From DE 10 2013 210 998 A1 is known a syringe body having an axial inner cavity, and a needle, which is connected to the syringe body, wherein the syringe body has a coupling segment at the needle-side longitudinal end of the syringe body, to which coupling segment the needle is fastened by means of a connecting element that can be slid on in the longitudinal direction. A radially inward cavity is provided on the coupling segment, which cavity can be brought into engagement or is in engagement with at least one corresponding locking segment provided on the connecting element. A special design of the syringe is required in order to form the connecting element.

From U.S. Patent Application Publication No. 2010/00167829 A1 is known a further apparatus for limiting the movement of a needle assembly when coupled to a medicament container.

From U.S. Pat. No. 5,925,032 A is known a syringe cannula holder, having a split outer sleeve that can be folded around the cannula. The sleeve is held in place by a sliding retaining nut, wherein a locking retainer holds the syringe within the sleeve. The assembly of the syringe and the cannula holder is complex.

From EP 1 521 608 B1 is known an accessory for a syringe for avoiding detachment of a needle from the syringe. The accessory includes a body of semi-tubular shape for receiving the syringe. Two transverse walls are provided in order to accommodate the proximal flange or proximal lateral tabs of the body of the syringe.

From WO 2005/065753 A1 is known a cylindrical cannula hood for a syringe for securing a cannula assembly to a syringe body. The cannula hood includes a cylindrical portion and a tapered portion, wherein the cylindrical portion is designed to fit over the syringe body and to be retained by a friction fit.

From U.S. Pat. No. 5,759,178 is known a support member for stabilizing the connection of a needle and a syringe in order to avoid breakage of the nozzle of the syringe.

From EP 1 971 382 B1 is known an accessory for a needle of a syringe comprising a sleeve surrounding the hub and comprising arms for locking the sleeve in position, wherein this locking mechanism includes latching pawls and shoulders. The safety needle accessory protects a user from needle stick injuries.

From U.S. Pat. No. 1,524,242 A is known a retaining helix spring as a part of a needle retaining assembly for syringes for avoiding detachment of a needle from a syringe. The accessory includes a syringe barrel having a discharge nipple and a helical spring resiliently engaging at its inner end the base of the nipple.

From U.S. Pat. No. 4,490,142 A is known a syringe with a pair of clamping arms that are mounted on a ring located at the front end of a syringe frame and are biased toward closed position for preventing accidental displacement of the needle hub. The clamping mechanism is complex and requires different components, e.g. a lever member. From U.S. Pat. Nos. 2,806,473 A, 4,822,343 A, WO 1990/011789

A1, and EP 3 187 218 A1 similar mechanisms are known. Such syringes are often used as blood collection devices.

Most of the accessories and methods mentioned above are very sophisticated in their structure and therefore, costly in their production, and/or they include a huge number of components that have to be handled, and/or the assembly of the accessories is time-intensive when adding to a conventional syringe-needle assembly, and/or the accessories require specific and complex tools for mounting on a syringe-needle assembly.

Further problems may occur when the needle has to be replaced during or to be removed after an application process or after a medical treatment. A cosmetic treatment, for example, may involve multiple single injections, which may require replacing the needle by a fresh needle after some injections and during the cosmetic treatment.

What is needed in the art is not only a safe connection of the syringe and the needle that prevents the risk of needle detachment during the injection, but also the possibility to simply and quickly replace a used needle. The replacement and/or the removal of a used needle from the injector should be a safe process for the operator, preventing the operator from being stuck by a needle, in particular preventing the operator from being stuck by a used needle. The previously mentioned accessories and methods require an operator to directly touch and contact a needle during dismantling, which can be a big danger for the operator because of being stuck by the needle.

SUMMARY OF THE INVENTION

Exemplary embodiments disclosed herein provide an apparatus for injecting a fluid including an injector for injecting a fluid and a needle assembly, including a needle and a hub for mounting the needle to the injector. The needle is attached to the injector for injecting the fluid in a safe way.

Exemplary embodiments provided according to the present invention can prevent the detachment of the needle from the injector when injecting a fluid, regardless of the compression force applied to the fluid and/or the viscosity of the fluid.

Exemplary embodiments disclosed herein provide an apparatus for injecting a fluid where needles of any sufficient diameter, in particular needles with a small diameter of the inner channel, can be used. Such needles typically are characterized by the diameter of the inner channel or bore, wherein the unit "Gauge" is normally used. Exemplary embodiments disclosed herein allow employing needles having a small diameter of the inner channel, e.g. in a range of a 31 Gauge needle, a 32 Gauge needle, a 33 Gauge needle or a 34 Gauge needle.

Exemplary embodiments disclosed herein provide an apparatus for injecting a fluid where an operator can simply and quickly replace the needle.

Exemplary embodiments disclosed herein provide an apparatus for injecting a fluid where a replacement of the needle can be performed, which prevents the operator from being stuck by the needle, in particular preventing the operator from being stuck by a used needle.

Exemplary embodiments disclosed herein provide an apparatus for injecting a fluid providing a visible evidence that the needle assembly is correctly mounted onto the injector so that the apparatus is ready and safe for an application or an injection.

In some exemplary embodiments provided according to the present invention, an apparatus for injecting a fluid includes: an injector configured to inject a fluid, the injector having a cylindrical container configured for receiving and containing the fluid, a coupling portion, and a peripheral section; a needle assembly including a needle and a hub, the hub defining a contact area, the coupling portion being configured to be coupled with the hub; and a needle retention device including a needle-retainer portion having at least one finger configured to radially extend over at least a part of the contact area of the hub, a container-contact portion defining a first opening configured to be attached in a form-fitting way onto the peripheral section of the container. When the apparatus is in its operational state for injecting a fluid, the hub of the needle assembly is coupled to the coupling portion of the container, the container-contact portion is attached to the container, and the at least one finger of the needle-retainer portion extends over at least a part of the contact area of the hub when the needle retention device is in its retaining position.

In some exemplary embodiments provided according to the present invention, a needle retention device for an injection apparatus includes: a needle-retainer portion including at least one finger configured to radially extend over at least a part of a contact area of a hub of a needle assembly and a container-contact portion defining a first opening configured to be attached in a form-fitting way onto a peripheral section of a container of an injector of the apparatus. The at least one finger is movable from a first position to a second position and is configured to lock the hub in the second position and unlock the hub in the first position.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figure 1:
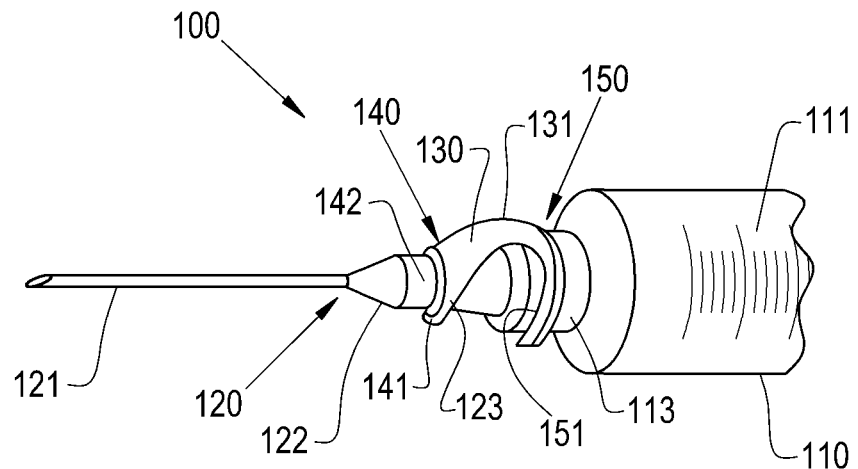
FIG. 1 is a perspective view of a detail of an exemplary embodiment of an apparatus for injecting a fluid including an injector for injecting a fluid, a needle assembly and a needle retention device, provided according to the present invention.

As used in this specification, the term "injecting a fluid" generally refers to application processes, e.g. in the chemical industry, or treatment processes such as medical or cosmetic treatments, where a fluid is injected into a body or object, once or several times, such as with the apparatus for injecting the fluid including an injector for injecting the fluid, such as a syringe, and a needle assembly.

Therefore, the fluid may include liquids, gases, solids or mixtures of these. In particular, the fluid may be a liquid or semi-liquid material or a pasty or highly viscous sub stance.

The needle assembly may include a needle and a hub defining a contact area, such as a shoulder.

The injector may include an axial inner cavity or cylindrical container, which extends in the direction of a longitudinal axis of the injector body and in which a plunger can be or is accommodated in such a way that the plunger can be moved in the longitudinal direction. The cylindrical container is configured for receiving and containing the fluid.

The container may have a proximal end which limits the chamber at one side and into which the plunger can be inserted, and an opposite distal end, which can include a mouth or a conically tapering tip. The distal end may be generally of an elongate shape tapering conically towards the distal end and may have an opening in the form of a channel through which the fluid can be discharged out of the container if a suitable plunger movement takes place in a longitudinal direction.

As used in this specification, the terms "proximal" and "distal" refer to the direction closer and away from an operator when using the apparatus, respectively. The operator can be a doctor or a nurse, for example, administering the preparation to a patient, or in any other way. It should be understood that this directional relationships are reversed when a patient administers a drug himself.

In the pharmaceutical field, such injectors are known as syringes and can be made of glass or polymer.

The injector may further include a coupling portion, configured to be coupled with the hub of the needle assembly. The coupling portion may include the conically tapering tip and/or any other structure to couple a hub of a needle assembly, for example a thread.

When the apparatus is in its operational state for injecting a fluid, the hub of the needle assembly is coupled to the coupling portion of the injector. In this manner, the needle of the needle assembly can be or is connected to the distal end of the container of the injector. When mounted, the needle of this so-called injector-needle assembly is configured to convey the fluid from the container to the patient's body through the channel or bore of the needle. Accordingly, the hub is fluid-tight connected to the coupling portion of the injector. In some embodiments, the connection of the needle assembly and the injector is made such that the connection can withstand a highly pressurized fluid.

To discharge the fluid out of the container, the plunger can be moved in a longitudinal direction towards the distal end of the container. This can be done by an operator or in any other way, e.g. by or with support of any kind of mechanical devices such as a stepper motor. The movement applies the necessary compression force to the fluid stored in the container, so that the fluid can be conveyed outwards, for example to a patient's body, via the needle.

In accordance with some embodiments provided according to the present invention, the hub can be fastened by a connecting element that can be slid on the mouth of the injector in the longitudinal direction.

In some embodiments, the hub can be coupled to the injector by a thread, for example by a Luer lock connector. In accordance with such embodiments, the coupling portion of the injector and the hub of the needle assembly each may include a Luer lock connector in accordance with the international standard ISO 80369. Typically, the injector includes a so-called female Luer lock connector, and the needle assembly includes a so-called male Luer lock connector. The hub and the coupling portion can be or are coupled via the respective Luer lock connectors. The coupling of the hub to the injector by a thread, such as by a Luer lock connector, guarantees the compatibility between different manufacturers of needles, needle assemblies and injectors, and, therefore, makes it possible to use the present invention for a large number of needles, needle assemblies and injectors.

The needle assembly and the injector can be coupled easily without any tools if such a Luer lock connection is available. For injecting the fluid, as mentioned previously, a compression force can be applied to the fluid stored in the container in order to discharge the fluid through the distal end of the container and through the inner channel of the needle.

In accordance with some exemplary embodiments provided according to the present invention, there is provided the needle retention device, including a needle-retainer portion, having a finger configured to radially extend over at least a part of the contact area of the hub, and a container-contact portion, defining a first opening configured to be attached onto a peripheral section of the container, such as in a form-fitting way.

When the hub of the needle assembly is coupled to the coupling portion of the container, the container-contact portion is attached to the container and the finger of the needle-retainer portion extends over at least a part of the contact area of the hub when the needle retention device is in its retaining position, such as for preventing a detachment of the needle assembly from the container. In some embodiments, the contact area of the hub may include a shoulder or any other kind of a recess, configured such that the finger of the needle-retainer portion so that the finger can snap in the shoulder or the recess.

The apparatus for injecting a fluid, including the needle retention device, offers an easy to handle and time-saving way for safely connecting a needle with an injector.

When adding the needle retention device to an injector-needle assembly, no tools are required.

The connection of the injector and the needle is secured by the needle retention device that prevents, when attached to the injector-needle assembly, the risk of needle detachment during the injection.

The needle retention device provided in accordance with the present invention prevents the detachment of the needle from the injector when injecting a fluid, regardless of the compression force applied to the fluid and/or the viscosity of the fluid.

The present invention allows using needles of any diameter, in particular the use of needles having a small diameter of the inner channel. Characterized by the diameter of the inner channel in the unit "Gauge", the present invention makes it possible to employ very thin needles, for example small-bore needles having a size of the inner channel of less than or equal to that of a 30 Gauge needle, a 31 Gauge needle, a 32 Gauge needle, a 33 Gauge needle or a 34 Gauge needle.

Thus, the present invention allows the use of injectors having a volume of, for example, 0.25 mL, 0.5 mL, 0.6 mL, 1.0 mL, 1.2 mL, 1.5 mL, 2.0 mL, 2.25 mL, 3, 0 mL, 5.0 mL, 10.0 mL, 20 mL or 50 mL, together with cannulas or needles of different Gauge sizes, e.g. 27, 28, 29, 30 Gauge and in particular with needles with Gauge sizes 31, 32, 33, or 34 Gauge.

The needle retention device additionally offers the possibility to simply and quickly remove a used needle and/or replace a needle by another needle. Such replacements may occur during an application or treatment process. For cosmetic treatments, for example, it may be necessary to involve multiple single injections, which may require replacing a used needle after some injections by a fresh needle.

The needle retention device provides a secure replacement or removal of a needle and/or a secure assembly of a needle to the injector for an operator, preventing the operator of being stuck by a needle, in particular preventing the operator of being stuck by a used needle.

If the needle is connected to the syringe with a thread, for example with a Luer lock connection that is widespread in the pharmaceutical field, a great advantage of the present invention lies in the fact that independent from the number of needle replacements, any needle is attached and secured in the same manner. This might be important since the removal of a used needle from an injector may pollute the thread with the fluid, at least to a small extent, when the fluid is leaked out of the container of the injector and/or out of the inner channel of the needle. But, if the thread is polluted with fluid, the frictional forces will be worse, e.g. the torque to loosen the connection can be significantly reduced. This may lead to a high risk for detachment of the needle during an injection.

The present invention therefore allows several replacements of the needle without increasing the risk for a needle detachment since the needle is held by the needle retention device.

Therefore, the one or more needle replacements can take place even during an application or treatment process. Thus, the present invention allows the operator to save, simply and quickly remove and/or replace the needle of the injector.

The needle retention device may include an elongated portion, which may extend parallel to a longitudinal axis, that may connect the needle-retainer portion and the container-contact portion to each other.

To improve the gripping by the operator, in some embodiments the elongated portion is arranged such that it protrudes radially in order to allow an operator to hold the needle retention device in a safe way. Therefore, in some embodiments the elongated portion does not, at least in sections, touch the outer portion of the hub or the container, but may protrude by a few millimeters from these surfaces in order to allow an operator a better handling of the needle retention device.

When the needle retention device is firmly connected to the needle assembly, the operator can easily handle the needle retention device together with the needle assembly and the needle, respectively. Accordingly, mounting and/or detaching the needle retention device and/or of the needle assembly becomes very easy and safe. The elongated portion may therefore include additionally any kind of a finger grip.

This makes it very helpful for the handling of used needles, because the needle, in particular a used needle, does not have to be touched by the operator. This is also very helpful when the needle is attached via a thread to the injector, since in such cases the needle has to be rotated to release the connection.

In accordance with such embodiments, the present invention thus enables an easy separation and disposal of used needles. Since the needle retention device is a very cost-efficient product, the used needle can be disposed very easy together with the needle retention device, when the needle retention device is attached to the needle assembly. In order to improve further recycling activities, it could be helpful if the needle retention device is made of the same material or material group as the hub of the needle assembly.

The needle retention device is an easy to produce and cost-efficient accessory that can be made from a plastic material by injection molding, e.g., or 3D-printing. It can be made monolithically in one-piece.

The needle retention device may include a thermosetting or a thermoplastic material adapted to pharmaceutical applications. In some embodiments, the material for the needle retention device is selected to provide a specific degree of elasticity. This allows the needle retention device to absorb higher forces in the axial direction that might occur when the fluid is very pasty or highly viscous. The yield strength that can be measured in accordance with DIN EN ISO 527-1 may be in the range of at least 30 $N/mm^2$ or in the range of at least 40 $N/mm^2$.

The needle retention device can be made of thermoplastics, including but not limited to those commonly used and approved in the medical field, accordingly including cyclo-olefin copolymer (COC), cyclo-olefin polymer (COP), acrylonitrile-butadiene-styrene (ABS), polyamide (PA), polylactate (PLA), polymethyl methacrylate (PMMA), polycarbonate (PC) or polyethylene terephthalate (PET). The yield strength of PA, for example, may be in a range of approximately 50 to 80 $N/mm^2$, the yield strength of PC may be in a range of 60 $N/mm^2$ or more.

The needle retention device also can be made of thermoset plastics, including but not limited to those commonly used and approved in the medical field, accordingly including or consisting of cellulose acetate (CA) or transparent thermosetting resin.

In some embodiments, the material for the needle retention device is further selected to be stable to the procedures of sterilization, e.g. stable when exposed to an autoclave or to methods of X-ray sterilization. Depending on the preparation, it is then also possible to sterilize a filled, in particular prefilled, injector together with the preparation, which can considerably contribute to an improved storage life, since in this case germs within the container can generally be excluded with high yield.

According to another aspect of the present invention, it is advantageous if the assemblies described above are X-ray or gamma-ray stable and thus accessible to X-ray or gamma-ray sterilization, which reliably precludes bacterial contamination of the prefillable or prefilled container.

In another embodiment provided according to the present invention, the assemblies are temperature stable up to 121° C. and can therefore be autoclaved.

In some embodiments, the color of the needle retention device may be, at least partially, a signal color, which may be different from the color of the container and/or the needle and/or the hub. This provides a safety feature of the apparatus because the operator quickly can check whether the needle is secured in order to prevent detachment. The color can be selected in accordance with the norm RAL in order to clearly identify safety features. For example, the needle retention device can be colored, at least in sections, in accordance with the color RAL 1023 ("safety yellow").

In some embodiments, the needle retention device can only be attached to the injector-needle assembly if the needle assembly is completely and correct coupled to the injector. For example, this can be made such that the contact area of the hub may include a recess, configured such that the finger of the needle-retainer portion only can snap in when the hub is correctly mounted onto the injector. This provides an additional safety feature to the operator, because the operator can quickly check whether the needle is correctly attached to the injector. The present invention therefore offers a visible evidence that the needle assembly is correctly and safely mounted to the container before the delivery of the fluid.

Thus, the present invention offers a visual perception for the operator that the needle assembly is safely coupled to the coupling portion of the container and secured against detachment when the needle retention device is attached to the injector-needle assembly.

In some embodiments, the needle-retainer portion includes at least two fingers defining a second opening configured for circumferentially engaging the contact area of the hub.

For such embodiments, the hub may include a contact area in the form of a shoulder, located between a distal end portion and a proximal end portion of the hub. The fingers may snap into the contact area, such as the shoulder, of the hub in order to counteract an axial movement of the hub when the hub is coupled to the injector. In this manner, a detachment of the needle assembly can be prevented.

In some embodiments, the second opening defines an inner diameter smaller than the outer diameter of the contact area, such as the shoulder, such that the two fingers can snap onto the contact area, such as the shoulder, to form a form-fitting or a snap fit in radial direction when mounted. This allows a firm fit of the needle retention device on the hub or the needle assembly, respectively.

Such a firm fit results in an advantage of the present invention, because for removal of the needle, or the needle assembly, respectively, the operator only has to hold on to the needle retention device. Therefore, the operator is, when removing the needle or the needle assembly, not into contact with the needle or the needle assembly. This increases the safety for the operator and prevents the operator from being stuck by the needle when removing the needle.

In some embodiments, the first opening of the container-contact portion completely encloses a peripheral section of container. This allows a firm fit of the needle retention device onto the injector. The needle retention device can be assembled to the injector by sliding in a longitudinal direction up to the intended position. The needle retention device can be held in place by latching in an opposite recess, if available on the peripheral section of the container. The needle retention device can also be attached to the peripheral section of the container by adhesives.

In some embodiments, the needle retainer portion of the needle retention device includes more than one finger arranged parallel to each other and being spaced apart from each other, such as defining equal distances to each other. The fingers may be arranged such that they extend, at least in sections, in a direction parallel to the longitudinal direction of the container. This allows the fingers to encompass a peripheral section of the hub of the needle assembly in a longitudinal direction. The end of the fingers may include a radially projecting hook directed inwards to engage the contact area of the hub when mounted on the injector. In this way, several holding points for preventing axial detachment of the hub can be provided.

A very stable and evenly in axial direction holding mechanism of the hub can be achieved if the needle retainer device include more than two such fingers, defining equal distances to each other, and in accordance providing evenly distributed holding positions over the circumference of the contact area. In some embodiments, three such fingers, four fingers, five fingers or six fingers or even more are provided.

In some embodiments, the needle retention device may further include a locking ring, defining an opening configured for circumferentially enclosing, at least in sections, the container-contact portion of the needle retention device. For such embodiments, the needle retainer device may include at least two such fingers arranged parallel to each other and being spaced apart from each other, such as defining equal distances to each other and arranged such that they extend, at least in sections, in a direction parallel to the longitudinal direction of the container.

In such embodiments, the locking ring is configured for rotating around the axis of the container when mounted, having recesses for receiving the fingers when in a first, opened position when the fingers do not extend over the contact area of the hub, such as the shoulder of the hub, and pressing the fingers onto the shoulder when in a second, closed position. Mechanically acting stops or inter-engaging latches may be provided to form an end stop at the first and second rotational positions.

In some embodiments, the needle retention device further includes a sliding ring, defining an opening configured for circumferential enclosing, at least in sections, the container-contact portion of the needle retention device. Also, for such embodiments, the needle retainer device may include at least two such fingers arranged parallel to each other and being spaced apart from each other, such as defining equal distances to each other and arranged such that they extend, at least in sections, in a direction parallel to the longitudinal direction of the container.

In such embodiments, the sliding ring is configured for axial movement along the axis of the container when mounted, releasing the fingers when in a first axial position, and pressing the fingers into the contact area of the hub, such as the shoulder of the hub, when in a second axial position.

In some exemplary embodiments provided according to the present invention, an apparatus for injecting a fluid includes an injector for injecting the fluid, such as a syringe for injecting a medical, a diagnostic, a cosmetic or a dental preparation, a needle assembly and a needle retention device. The container of the apparatus is filled, completely or at least to a small amount, with a fluid. The fluid may be, for example, a medical, a diagnostic, a cosmetic or a dental preparation.

The fluid may include preparations suitable for use in the hyaluronic acid segment for cosmetics, medical or opthalmics applications, for example.

The fluid may include preparations suitable for use in the veterinary segment for anti-parasite applications, for example.

The fluid may include preparations suitable for use in the infusion therapy segment for infusion therapy applications, for example.

The fluid may include preparations suitable for use in the neuroleptics segment for schizophrenia medication, for example.

The fluid may include preparations suitable for use in the biologics segment for biotech, sensitive molecules or sensitive protein applications, for example.

The fluid may include preparations suitable for use in other segments too, for diluent or cancer treatment, for emergency drugs or for vaccines, for example.

In some exemplary embodiments provided according to the present invention, a needle retention device for an apparatus for injecting a fluid includes an injector for injecting a fluid, such as a syringe for injecting a medical, diagnostic, cosmetic or dental preparation, including a needle-retainer portion, having a finger configured to radially extend over at least a part of a contact area of a hub of a needle assembly when coupled to a container of an injector of the apparatus, and a container-contact portion, defining a first opening configured to be attached in a form-fitting way onto a peripheral section of the container of the injector.

When the needle assembly is coupled to a coupling portion of the injector, the container-contact portion is attached to the container and the finger of the needle-retainer portion extends over at least a part of the contact area of the hub when the needle retention device is in its retaining position, such as for preventing a detachment of the needle assembly from the container.

The present invention provides, in some embodiments, the use of an apparatus for injecting a fluid including an injector for injecting a fluid, such as a syringe for injecting a medical, diagnostic, cosmetic or dental preparation.

When using the apparatus for injecting the fluid, the fluid may have a viscosity in a range of at least 1 mPa*s, such as of at least 10 mPa*s, 12 mPa*s, or 15 mPa*s.

When using the apparatus for injecting the fluid, the needle of the apparatus may include small-bore needles having a size of the inner channel of less than or equal to that of a 30 Gauge needle, a 31 Gauge needle, a 32 Gauge needle, a 33 Gauge needle or a 34 Gauge needle.

When using the apparatus for injecting the fluid, the needle retention device may prevent a detachment of the needle assembly from the injector when injecting the fluid, the maximum force that can be applied to the fluid being at least 50 N, such as at least 70 N, at least 90 N, or at least 100 N.

The present invention thus also provides, in some embodiments, a method including injecting or applying a fluid from or with an apparatus provided in accordance with the present invention. The fluid may include liquids, gases, solids or mixtures of these. The fluid may be a liquid or semi-liquid material or a pasty or highly viscous substance.

For injecting the fluid, a needle assembly including a needle and a hub may be coupled to an injector, the container of the injector being configured for receiving and containing the fluid.

Specific injections require the fluid being pasty or having a high viscosity. For example, when injecting cosmetic preparations like Botulinum toxin, also called botulinum or botulinum neurotoxin, for beauty treatments, such preparations may have a viscosity in a range of at least 1 mPa*s.

In a similar way, applications such as medical treatments may include hyaluronic acid preparations that are injected into arthrosis-damaged joints of a body in order to lubricate the joint and act as a "shock absorber", for example. When injecting such hyaluronic acid preparations, the viscosity of the preparation may also be in a range of at least 1 mPa*s.

Also, fluids including a preparation in other segments as mentioned above may have such a similar viscosity.

In order to enable injections of such highly viscous fluids, the connection of the needle and the container is secured by the needle retention device provided according to the present invention such that the connection can withstand a highly pressurized fluid in the container. Thus, the needle retention device of the present invention prevents, when attached to an injector-needle assembly, the detachment of the needle or needle assembly, respectively, from the injector when injecting such fluids.

For injecting the fluid, a compression force is to be applied to the fluid stored in the container in order to discharge the fluid through the distal end of the container and through the inner channel of the needle. The compression force can be applied to the fluid by a movement of a plunger in a longitudinal direction from the proximal end to the distal end of the container. This can be done by an operator, for example. The movement of the plunger applies the necessary compression force to the fluid stored in the container, so that the fluid can be conveyed outwards, for example to a patient's body, via the needle.

The present invention enables injecting a fluid having a viscosity in a range of at least 1 mPa*s, such as of at least 10 mPa*s, 12 mPa*s, or 15 mPa*s. The viscosity may be measured with a viscometer in accordance with the norm EN ISO 3219.

Especially when such highly viscous liquids are used, the pressure to the fluid when moving the plunger may become relatively high very quickly. This danger is exacerbated when the needle assembly includes very thin needles, for example small-bore needles having a size of the inner channel of less than or equal to that of a 30 Gauge needle.

The present invention enables injecting a fluid from or with an apparatus provided in accordance with the present invention. The injector-needle assembly may be exposed to a pressurized fluid having a pressure of almost 5 bar, 10 bar, 15 bar or even 20 bar or more. Even under these conditions, the needle is not being detached from the injector.

The maximum force that can be applied to the fluid stored in the container of the apparatus provided in accordance with the present invention when injecting the fluid is up to at least 50 N, such as up to at least 70 N, up to at least 90 N, or up to at least 100 N, without detachment of the needle assembly from the injector.

A force of about 100 N is above the force of approximately 95 N for a male and approximately 64 N for a female normally reached when a male or a female operator, respectively, is using an apparatus provided in accordance with the present invention, e.g. a syringe, and is applying a force to the finger pad of the plunger. Therefore, the apparatus provided in accordance with the present invention safely resists the maximum forces that an operator manually can apply to the apparatus when pressing his finger against the finger pad in order to apply the compression force to the fluid.

At the same time, the present invention enables injecting a fluid from or with an apparatus provided in accordance with the present invention. The needles of the needle assembly include small-bore needles having a size of the inner channel of less than or equal to that of a 30 Gauge needle, a 31 Gauge needle, a 32 Gauge needle, a 33 Gauge needle or a 34 Gauge needle.

The present invention thus also provides, in some embodiments, a method including injecting a fluid from or with an apparatus provided according to the present invention, including a "ready-to-use" prefilled container, via a needle with a Gauge size equal to that of a 30 Gauge needle, a 31 Gauge needle, a 32 Gauge needle, a 33 Gauge needle or a 34 Gauge needle.

The present invention thus also provides, in some embodiments, a cosmetic method including injecting a cosmetic preparation using an apparatus provided according to the present invention. The container is prefilled with a liquid, such as with a cosmetic preparation, and in which the needle is having a Gauge size equal to that of a 30 Gauge needle, a 31 Gauge needle, a 32 Gauge needle, a 33 Gauge needle or a 34 Gauge needle.

In some embodiments, there is provided an apparatus for injecting a fluid including an injector for injecting a fluid, such as a syringe for injecting a medical, diagnostic, cosmetic or dental preparation, a needle assembly and a needle retention device. The needle assembly includes a needle and a hub that defines a contact area.

The injector includes a cylindrical container configured for receiving and containing the fluid, which may be a medical preparation, and a coupling portion configured to be coupled with the hub of the needle assembly. The needle retention device includes a needle-retainer portion having a finger configured to radially extend over at least a part of the contact area of the hub, a container-contact portion, defining a first opening configured to be attached onto a peripheral section of the container, such as in a form-fitting way. When the apparatus is in its operational state for injecting a fluid, the hub of the needle assembly is coupled to the coupling portion of the injector, the container-contact portion is attached to the container, and the finger of the needle-retainer portion extends over at least a part of the contact area of the hub when the needle retention device is in its retaining position, such as for preventing a detachment of the needle assembly from the container, the needle-retainer portion includes at least two fingers defining an opening configured for circumferentially engaging the shoulder of the hub and the needle retention device includes a thermosetting material or a thermoplastic material adapted to pharmaceutical applications.

Further details of the present invention will become apparent from the description of the illustrated embodiments.

The present invention provides an apparatus for injecting a fluid including an injector for injecting the fluid, such as a syringe for injecting a medical, a diagnostic, a cosmetic or a dental preparation, a needle assembly and a needle retention device.

Referring now to the drawings, and more particularly to FIG. 1, there is shown an exemplary embodiment of such an apparatus 100 provided according to the present invention for injecting a fluid, including an injector 110 for injecting the fluid, such as a syringe for injecting a medical, a diagnostic, a cosmetic or a dental preparation, a needle assembly 120 and a needle retention device 130. The fluid is a liquid or semi-liquid material or a pasty or highly viscous sub stance.

Figure 2:
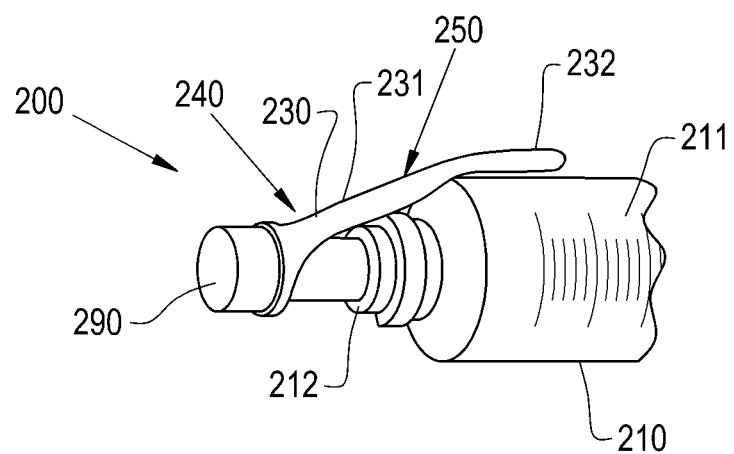
FIG. 2 is a perspective view of a detail of an exemplary embodiment of an apparatus for injecting a fluid, including an injector for injecting a fluid, a cap for closing a mouth of the injector, and a needle retention device, provided according to the present invention.

FIG. 2 is a perspective view of a detail of an apparatus 200 for injecting a fluid, comprising an injector 210 with a container 211 for injecting a fluid and a coupling portion 212, a cap 290 for closing the mouth of the injector 210, and a needle retention device 230, according to an exemplary embodiment provided according to the present invention.

The needle assembly 120, as shown in FIG. 1, includes a needle 121 and a hub 122. The hub 122 defines a contact area 123, such as a shoulder. In this example, the contact area 123 is constructed as a shoulder.

The injector 110 includes a container 111, which extends in the direction of a longitudinal axis of the injector body and in which a plunger can be accommodated in such a way that the plunger can be moved in the longitudinal direction. The cylindrical container 111 is configured for receiving and containing the fluid. In the illustrated example, the injector 110 is a syringe as typically used in the pharmaceutical field, having a container volume of 10 mL. The syringe is made of a polymer material. Such syringes can be supplied from the company SCHOTT AG, Mainz, under the name "TopPac SD", for example, in a huge variety of sizes.

The injector 110 further includes a coupling portion, configured to be coupled with the hub 122 of the needle assembly 120.

When the apparatus 100 is in its operational state for injecting a fluid, as shown in the embodiment of FIG. 1, the hub 122 of the needle assembly 120 is coupled to the coupling portion of the injector 110. This injector-needle assembly of FIG. 1 is therefore ready for an injection.

Regarding the apparatus 100 of FIG. 1, the connection of the needle 121 and the container 111 is made such that the connection can withstand a highly pressurized fluid in the container 111. To discharge the fluid out of the container 111, a plunger can be moved in a longitudinal direction towards the distal end of the container. This can be done by an operator or in any other way, e.g. by a mechanical device like a stepper motor. Such a movement applies the compression force to the fluid stored in the container, so that the fluid can be conveyed outwards, for example to a patient's body, via the needle 121.

In accordance with the embodiment of FIG. 1, the hub 122 is fastened by a connecting element to slide on the mouth of the injector 110 in a longitudinal direction.

In another exemplary embodiment provided according to the present invention, the hub 22 can be coupled to the injector 10 by a thread, for example by a Luer lock connector. An injector 10, also suitable for the present invention and including such a Luer lock connection, can be seen in FIGS. 3 and 4, for example.

Figure 3:
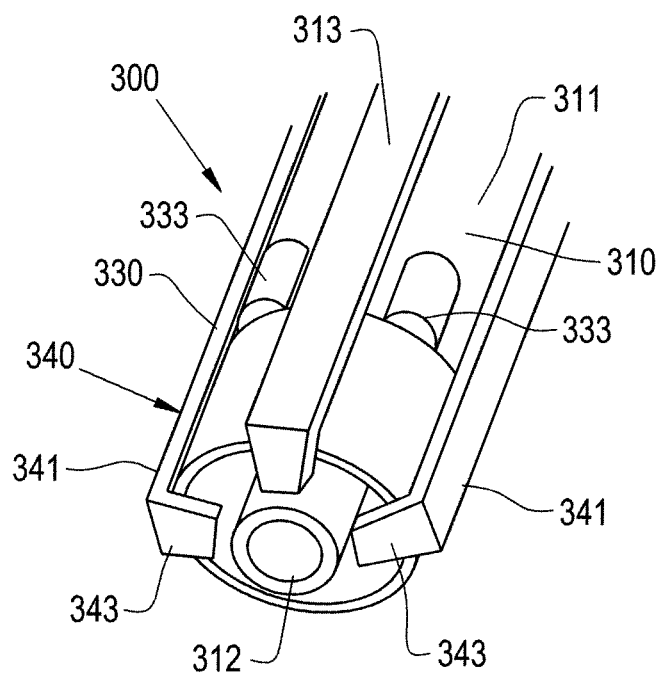
FIG. 3 is a perspective view of a detail of an exemplary embodiment of an apparatus for injecting a fluid, including an injector for injecting a fluid and a needle retention device having several elongated fingers, the injector including a Luer lock connector, provided according to the present invention.

FIG. 3 is a perspective view of a detail of an apparatus 300 for injecting a fluid, including an injector 310 with a container 311 for injecting a fluid and a needle retention device 330 having several elongated fingers 341. The injector 310 includes a Luer lock connector, according to an exemplary embodiment provided according to the present invention, and a peripheral section 313. The embodiment of the needle retention device 330 of FIG. 3 includes embedded bumps 333 on the container for rotationally opening the fingers 341.

Figure 4:
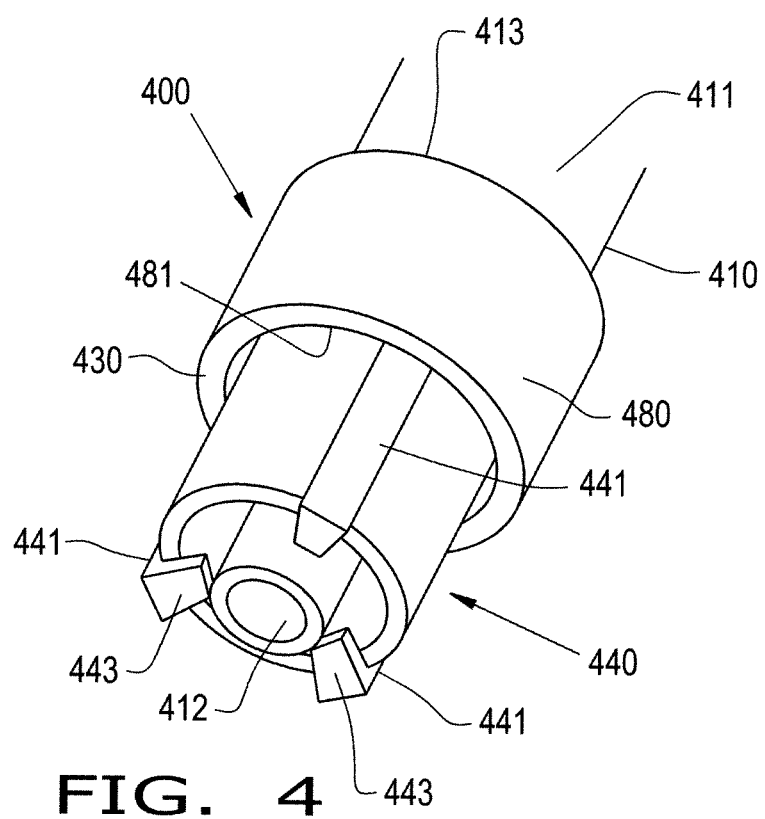
FIG. 4 is a perspective view of a detail of an exemplary embodiment of an apparatus for injecting a fluid, including an injector for injecting a fluid and a needle retention device having several elongated fingers and a sliding ring, provided according to the present invention.

FIG. 4 is a perspective view of a detail of an exemplary embodiment of an apparatus 400 for injecting a fluid, including an injector 410 for injecting a fluid and a needle retention device 430 having several elongated fingers 441 and a sliding ring 480, provided according to an exemplary embodiment of the present invention. The opening of the struts or fingers 441 is performed by rotation and/or axial movement of the sliding ring 480. The injector 410 includes a peripheral section 413.

As shown in the embodiments of FIGS. 3 and 4, the coupling portion 312, 412 of the injector 310, 410 and the hub of the needle assembly each include a Luer lock connector in accordance with the international standard ISO 80369. The hub and the coupling portion 312, 412 are coupled via the Luer lock connectors.

The coupling of the hub to the injector 310, 410 by such a Luer lock connector guarantees the compatibility between the different manufacturers of needles, needle assemblies, and injectors, and, therefore, makes it possible to use the present invention for a large number of needles, needle assemblies, and injectors 10.

In accordance with one aspect of the present invention and as shown in FIG. 1, there is provided a needle retention device 130, including a needle-retainer portion 140, having a finger 141 configured to radially extend over at least a part of the contact area 123 of the hub 122, and a container-contact portion 150, defining a first opening 151 configured to be attached onto a peripheral section 113 of the container 111, such as in a form-fitting way. The needle-retainer portion 140 and the container-contact portion 150 are connected to each other by an elongated portion 131, arranged in a longitudinal direction.

As also shown in FIG. 1, the hub 122 of the needle assembly 120 is coupled to the coupling portion 112 of the injector 110 representing an injector-needle assembly. The needle retention device 130 is attached to this injector-needle assembly in its retaining position. The container-contact portion 150 is attached to the container 111 and the finger 141 extends over at least a part of the contact area of the hub 122. In this manner, the needle retention device 130 prevents a detachment of the needle assembly 120 from the injector 110.

The apparatus 100 for injecting a fluid in accordance with the present invention offers an easy to handle and time-saving way for safely connecting a needle 121 with an injector 110 by providing the needle retention device 130.

When adding the needle retention device 130 to an injector-needle assembly, no tools are required.

The connection of the injector 110 and the needle 121 is secured by the needle retention device 120 that prevents, when attached to the injector-needle assembly, the risk of needle detachment during an injection or an application or treatment process.

The needle retention device 130 provided in accordance with the present invention prevents the detachment of the needle 121 from the injector 110 when injecting a fluid, up to very high compression forces applied to the fluid and/or the viscosity of the fluid.

It was shown in comparative tests that a force of approximately 105 N, corresponding to a pressure of the fluid in the container of approximately 33 bar, can be applied to a 1 mL glass syringe that is filled with the fluid. The syringe is combined with a standard needle from the supplier "Terumo", without a needle pop off. Only leakages have been observed.

In further tests, it was shown that syringes made of polymer, e.g. "TopPac HVD" from SCHOTT AG, have better characteristics in terms of needle pop off and leakage than needles made of glass.

In additional tests it was shown for apparatuses, including such syringes made of a polymer material, that the mean value for leakage and needle pop off is between 1.6 and 2.3 times better when using the needle retention device provided according to the present invention.

The present invention allows using needles 121 of any diameter, in particular the use of needles 121 having a small diameter of the inner channel, making it possible to employ very thin needles 121, for example small-bore needles 121 having a size of the inner channel of less than or equal to that of a 30 Gauge needle, a 31 Gauge needle, a 32 Gauge needle, a 33 Gauge needle or a 34 Gauge needle.

Thus the present invention allows the use of injectors 110 having a typical volume of, for example, 0.25 mL, 0.5 mL, 0.6 mL, 1.0 mL, 1.2 mL, 1.5 mL, 2.0 mL, 2.25 mL, 3, 0 mL, 5.0 mL, 10.0 mL, 20 mL or 50 mL, together with cannulas or needles 121 of different Gauge sizes, e.g. 27, 28, 29, 30 Gauge and in particular with needles with Gauge sizes 31, 32, 33, or 34 Gauge.

The needle retention device 130 additionally offers the possibility to simply and quickly remove a used needle 121 and/or replace a needle 121 by another needle 121. Such replacements may occur during an application or treatment process. For cosmetic treatments, for example, it may be necessary to involve multiple single injections, which may require replacing a used needle 121 after some injections by a fresh needle 121.

The needle retention device 130 provides a secure replacement or removal of a needle 121 and/or a secure assembly of a needle 121 to the injector 110 for an operator, preventing the operator of being stuck by a needle 121, in particular preventing the operator of being stuck by a used needle 121.

The present invention is very advantageous for injector-needle assemblies, when the needle is connected to the injector 310, 410 with a thread, for example with a Luer-Lock connection as shown in FIGS. 3 and 4. In such cases, the removal of a used needle from an injector may pollute the thread by the fluid, at least to a small extent, when the fluid is leaked out of the container 311, 411 of the injector 310, 410 and/or out of the inner channel of the needle. If the thread is polluted with fluid, the frictional connection will be worse, e.g. the torque to loosen the connection can be significantly reduced. This may lead to a high risk for detachment of the needle during injection.

Therefore, the present invention offers an advantage because the detachment of the needle from the injector 310, 410 is prevented independent from the torque to loosen the connection. Thus, any needle is attached and secured in the same manner to the injector 310, 410.

The present invention allows the operator to save, simply and quickly remove and/or replace the needle 121 of the apparatus 100 at the end of use. For a good grip for an operator, in some embodiments the needle retention device 130 includes an elongated portion 131, which protrudes radially in order to allow an operator to hold the needle retention device 130 in a safe way.

Therefore, the elongated portion 131, as shown in FIG. 1, does not, at least in sections, touch the outer portion of the hub 122, but protrudes at least approximately 5 millimeters from the surfaces in order to allow an operator a better handling of the needle retention device 130. The elongated portion 131 may protrude from the outer surface of the hub 122 and/or the container 111 by at least 3 millimeters, such as at least 4 millimeters, at least 5 millimeters, at least 7 millimeters, or at least 10 millimeters. On the other hand, the handling of the complete apparatus 100 should not be adversely affected by such a protrusion, therefore the protrusion should be less than approximately 50 mm, such as less than 40 mm or less than 30 mm.

In a further exemplary embodiment provided according to the present invention, the needle retention device 230 includes an additional extended elongated portion 232 as shown in the embodiment of FIG. 2. The additional extended elongated portion 232 is made such that an operator can hold the needle retention device 230 securely. Of course, additional finger pads can be foreseen to improve the operator when gripping the needle retention device 230.

The great advantage is that for the handling of used needles 121, the needle 121, in particular a used needle 121, does not have to be touched directly by the operator. This is very helpful when the needle is attached via a thread to the injector 310, 410 as shown in the embodiments of FIGS. 3 and 4, for example, since in such cases the needle and/or the needle assembly has to be rotated compared to the container to release the connection. It is helpful if the elongated portion 131, 231 and/or the extended elongated portion 232 does not protrude more than 30 mm for a better handling when rotating.

Thus, the present invention enables an easy separation and disposal of used needles 121 or needle assemblies 120, respectively.

Since the needle retention device 130, 230, 330, 430 is a very cost-efficient product, the used needle 121 can be disposed very easy together with the needle retention device 130, 230, 330, 430 when the needle retention device is attached to the needle assembly.

The needle retention device 130, 230, 330, 430 is an easy to produce and cost-efficient accessory that can be made from a plastic material by injecting molding, e.g., or 3D-printing. The needle retention device 130, 230, 330, 430 is made monolithically in one-piece from cyclo-olefin copolymer (COC).

The needle retention device 130, 230, 330, 430 can be made of other thermoplastics, including but not limiting those commonly used and approved in the medical field, accordingly including cyclo-olefin polymer (COP), acrylonitrile-butadiene-styrene (ABS), polyamide (PA), polylactate (PLA), polymethyl methacrylate (PMMA), polycarbonate (PC) or polyethylene terephthalate (PET).

The needle retention device 130, 230, 330, 430 also can be made of thermoset plastics, including but not limiting those commonly used and approved in the medical field, accordingly including or consisting of cellulose acetate (CA) or transparent thermosetting resin.

The material for the needle retention device 130, 230, 330, 430 is selected to provide a specific degree of elasticity. This allows the needle retention device to absorb higher forces in the axial direction that might occur when the fluid is very pasty or highly viscous.

The material for the needle retention device 130, 230, 330, 430 is stable to the procedures of sterilization, i.e. the needle retention device 130, 230, 330, 430 is X-ray and/or gamma-ray stable and thus accessible to X-ray or gamma-ray sterilization, which reliably precludes bacterial contamination of the prefillable or prefilled container.

The material for the needle retention device 130, 230, 330, 430 is also temperature stable up to 121° C. and can therefore be autoclaved.

The needle retention device 130, 230, 330, 430 is colored in "safety yellow" (RAL 1023) in order to provide an additional safety feature of the apparatus 100, 200, 300, 400 because the operator quickly can check whether the needle 121 is secured for preventing detachment.

In some embodiments, the needle-retainer portion 140 includes two fingers 141 defining a second opening 142 configured for circumferentially engaging the contact area of the hub 122.

Such an embodiment is shown in FIG. 1, where the hub 122 includes a contact area 123 in the form of a shoulder, located between a distal end portion and a proximal end portion of the hub 122. The fingers 141 are disposed against the shoulder of the hub 122 in order to counteract an axial movement of the hub 122 when the hub 122 is coupled to the injector 110. In this manner, a detachment of the needle assembly 120 from the injector 110 can be prevented.

In the embodiments shown in FIGS. 3 and 4, the needle retainer portion 340, 440 of the needle retention device 330, 430 includes more than one finger 341, 441 arranged parallel to each other and being spaced apart from each other, such as defining equal distances to each other. The fingers 341, 441 may be arranged such that they extend, at least in sections, in a direction parallel to the longitudinal direction of the container 311, 411. This allows the fingers to encompass a peripheral section of the hub 322, 422 of the needle assembly 320, 420 in a longitudinal direction.

The end of the fingers 341, 441 further include a radially projecting hook 343, 443 directed inwards to engage the contact area of the hub 122 when mounted on the injector 310, 410. In this way, several holding points for preventing axial detachment of the hub 122 can be provided.

A very stable and evenly in axial direction holding mechanism of the hub 122 can be achieved if the needle retention device 330, 430 include more than two such fingers 341, 441, defining equal distances to each other, and in accordance providing evenly distributed holding positions over the circumference of the contact area. In the embodiments as shown in FIG. 4, e.g., three such fingers 441 are provided, defining three holding position distributed over the circumference of the contact area 123 of the hub 122.

Figure 5:
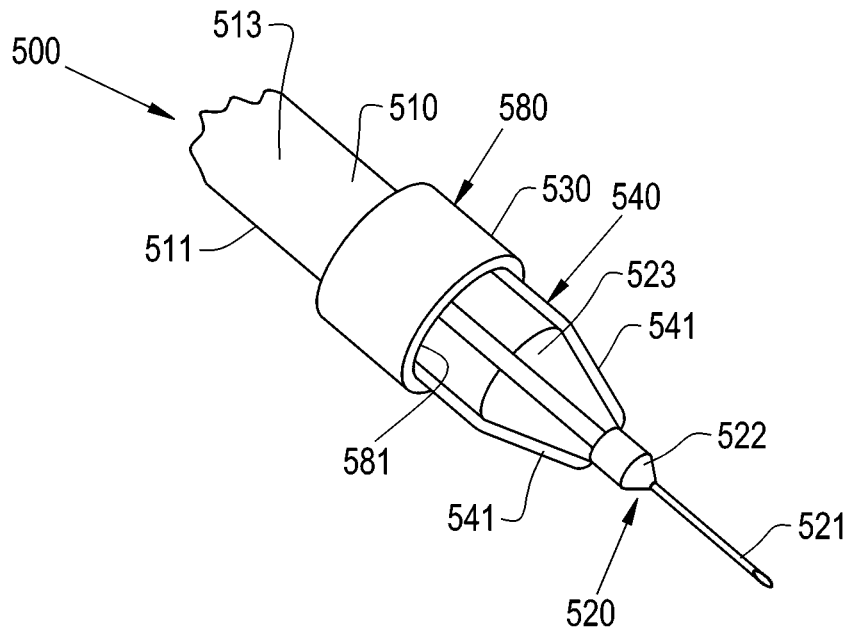
FIG. 5 is a perspective view of a detail of an exemplary embodiment of an apparatus for injecting a fluid, including an injector for injecting a fluid, the injector including a Luer lock connector, a needle assembly and a needle retention device having several elongated fingers and a sliding ring, provided according to the present invention.

In FIG. 5 is shown a perspective view of a detail of an exemplary embodiment of an apparatus 500 for injecting a fluid including an injector 510 with a container 511 for injecting a fluid. The injector 510 includes a container 511, a peripheral section 513, and a Luer lock connector, a needle assembly 520 with a needle 521, a needle retention device 530 with a needle-retainer portion 540 having several elongated fingers 541 and a sliding ring 580 with an opening 581, according to an exemplary embodiment of the invention.

Figure 6:
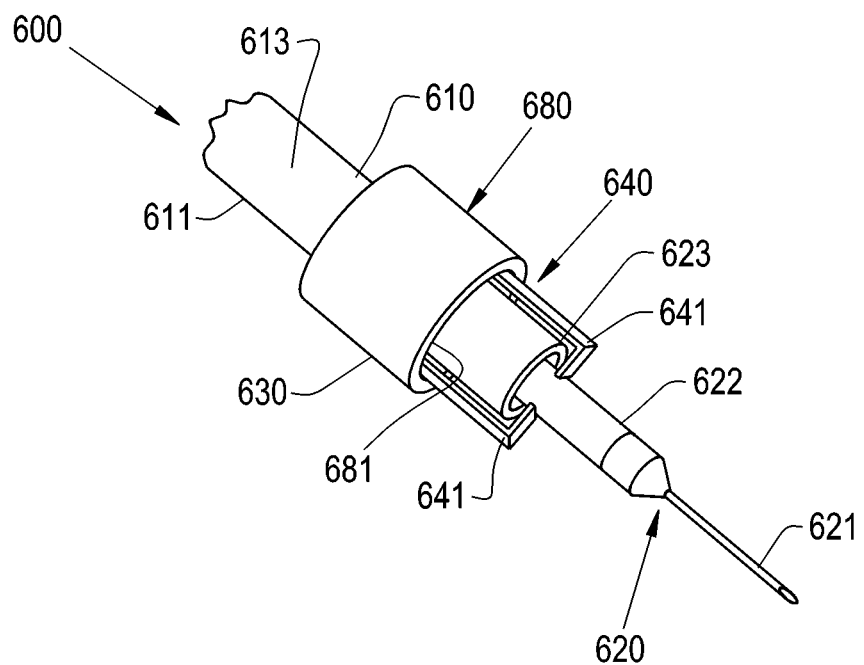
FIG. 6 is a perspective view of a detail of an exemplary embodiment of an apparatus for injecting a fluid, including an injector for injecting a fluid, the injector including a Luer lock connector, a needle assembly and a needle retention device having several elongated fingers and a sliding ring, in accordance with the embodiment of FIG. 4.

In FIG. 6 is shown a perspective view of a detail of a similar apparatus 600 with an injector 610 for injecting a fluid that includes a container 611 and a peripheral section 613, also including a Luer lock connector, a needle assembly 620 and a needle retention device 630 with a needle-retainer portion 640 having several elongated fingers 641 and a sliding ring 680 with an opening 681, in accordance with the embodiment of FIG. 4.

The needle retention device 630 of FIG. 6 includes two fingers 641. The needle retention device 530 in accordance with FIG. 5 includes four such fingers 541.

The sliding ring 580, 680 is configured for axial movement along the axis of the container 511, 611 when mounted, releasing the fingers 541, 641 when in a first axial position, and pressing the fingers 541, 641 into the contact area 523, 623 of the hub 522, 622, such as the shoulder of the hub 522, 622, when in a second axial position. FIGS. 5 and 6 show the sliding ring 580, 680 in the second axial position for locking the hub 522, 622 by pressing the fingers 541, 641 into the contact area 523, 623.

Figure 7A:
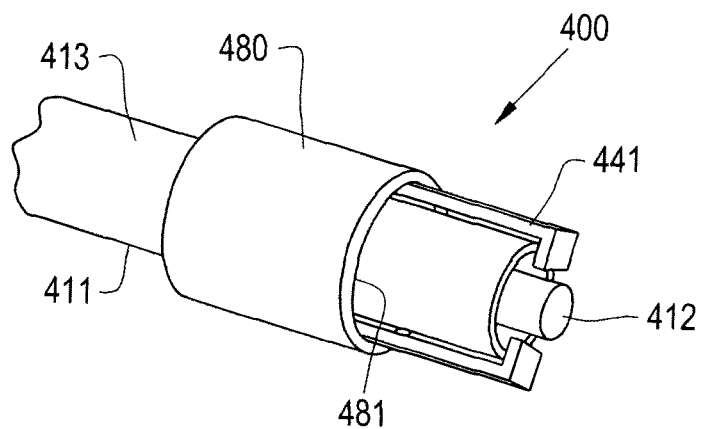
FIGS. 7A, 7B, and 7C are perspective views of a detail of an exemplary embodiment of an apparatus for injecting a fluid, including an injector for injecting a fluid, the injector including a Luer lock connector, and a needle retention device having several elongated fingers and a sliding ring, in accordance with the embodiment of FIG. 4, showing different positions of the sliding ring.
Figure 7B:
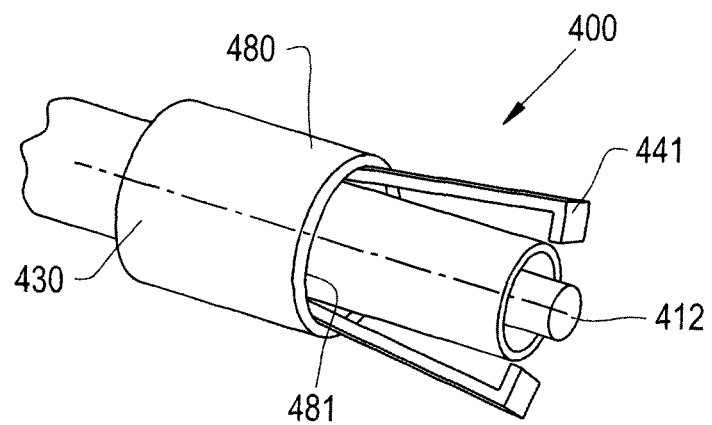
Figure 7C:
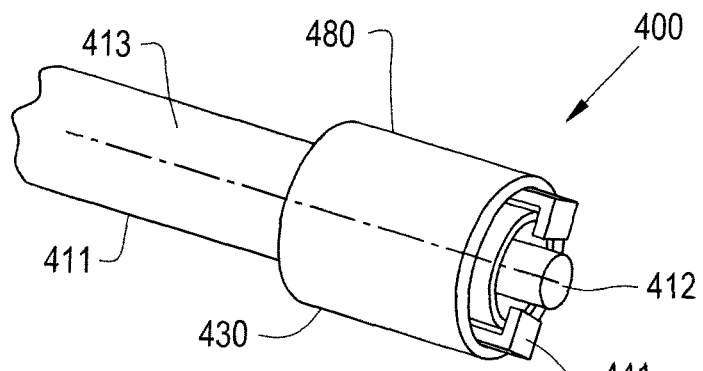

In FIGS. 7A, 7B and 7C are shown perspective views of a detail of an exemplary embodiment of an apparatus 400 for injecting a fluid in accordance with the embodiment of FIG. 4. The figures show different positions of the sliding ring 480.

The needle retention device 430 includes a sliding ring 480, defining an opening 481, also called an opening of the sliding ring 481, configured for circumferential enclosing, at least in sections, the container 411.

The opening 481 of the sliding ring 480 may be dimensioned such that it can completely enclose the container 411 with only a little radial tolerance, but enough to allow the necessary axial movement.

Also, for this embodiment, the needle retention device 430 may include at least two such fingers 441 as shown in FIGS. 7A, 7B and 7C, arranged parallel to each other and being spaced apart from each other, such as defining equal distances to each other and arranged such that they extend, at least in sections, in a direction parallel to the longitudinal direction of the container.

FIG. 7A shows a neutral position of the sliding ring 480, from which the sliding ring 480 can be axially moved in a proximal direction as shown in FIG. 7B or in a opposite direction to the distal end of the injector 410 as shown in FIG. 7C.

When in the proximal direction, corresponding to the first axial position, the sliding ring 480 enables the fingers 441 to open and to unlock the hub 422. As shown in FIG. 7B, the hook 443 of the fingers 441 can be removed radially outwards in this position of the sliding ring 480 for enabling a loosening of the hub.

As shown in FIG. 7C, the sliding ring 480 is in the second axial position, equivalent to a closed position, and thereby locking the hub by pressing the fingers 441 into the contact area.

As shown in this embodiment, the sliding ring 480 is configured for axial movement along the axis of the container 411 when mounted, releasing the fingers 441 when in a first axial position or open position, and pressing the fingers 441 into the contact area of the hub, such as the shoulder of the hub, when in a second axial position or closed position.

FIGS. 8A, 8B, 8C, 8D, 8E and 8F show different views of a detail of an exemplary embodiment of an apparatus for injecting a fluid, including an injector for injecting a fluid. The injector includes a container 811, a Luer lock connector, and a needle retention device having several elongated fingers 841 and a locking ring 870, according to an exemplary embodiment of the present invention, showing different positions of the locking ring 870. The locking ring 870 defines an opening 871, also called an opening of the locking ring, configured for circumferentially enclosing, at least in sections, the container 811.

Figure 8A:
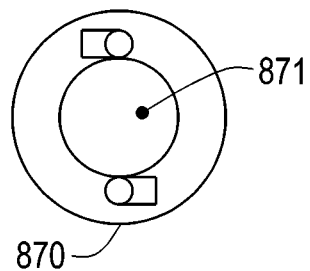
FIGS. 8A, 8B, 8C, 8D, 8E, and 8F are different views of a detail of an exemplary embodiment of an apparatus for injecting a fluid, including an injector for injecting a fluid, the injector including a Luer lock connector, and a needle retention device having several elongated fingers and a locking ring, provided according to the present invention, showing different positions of the locking ring.
Figure 8B:
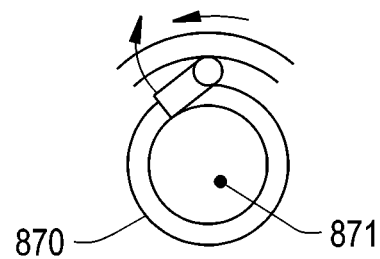
Figure 8C:
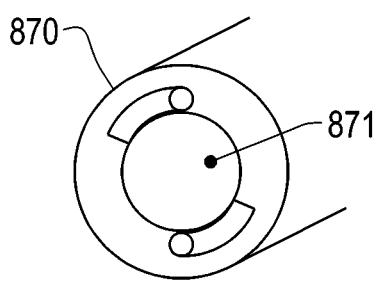
Figure 8D:
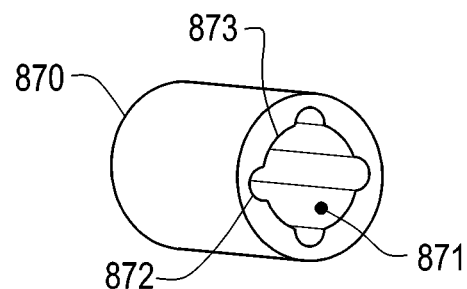
Figure 8E:
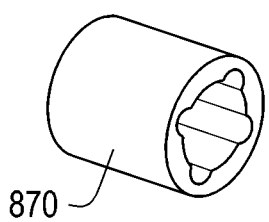
Figure 8F:
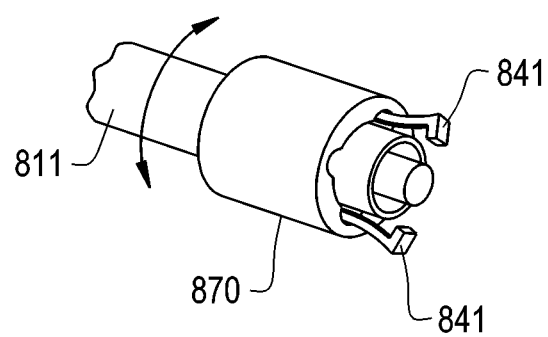

As best can be seen in FIG. 8F, the locking ring 870 interacts with the fingers 841 such that the locking ring 870 is configured for rotating around the axis of the container 811 when mounted, having recesses 872 in the inner wall of the opening 871 for receiving the fingers 841 when in a first, opened position when the fingers 841 do not extend over the contact area of the hub, such as the shoulder of the hub, and pressing the fingers 841 onto the contact area of the hub, such as the shoulder, when in a second, closed position. In some embodiments, the recesses 872 extend in an axial direction and are dimensioned such that they can, at least partially, include at least portions of the fingers 841.

Mechanically acting stops or inter-engaging latches may be provided to form an end stop at the first and second rotational positions of the locking ring 870.

As best can be seen in FIG. 8D, the inner wall of the opening 871 includes recesses 872 and protrusions 873. The number and the position of the recesses 872 corresponds to the number and the position of the fingers 841 in order to enable unlocking the fingers 841 when the locking ring 870 is in the opened position. Also, the number and the position of the protrusions 873 corresponds to the number and the position of the fingers 841 in order to press the fingers 841 onto the contact area of the hub, such as the shoulder, when the locking ring 870 is in the closed position.

FIGS. 8A-8C show the locking ring 870 in a front view, illustrating different arrangements of the protrusions 873 and the recesses 872.

For this embodiment, the needle retention device may include at least two such fingers 841 arranged parallel to each other and being spaced apart from each other, such as defining equal distances to each other and arranged such that they extend, at least in sections, in a direction parallel to the longitudinal direction of the container 811.

Figure 9A:
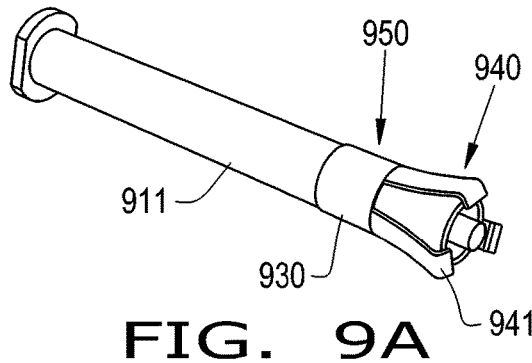
FIGS. 9A, 9B, 9C, 9D are perspective views of a detail of an exemplary embodiment of an apparatus for injecting a fluid, including an injector for injecting a fluid, the injector including a Luer lock connector, and a needle retention device having three elongated fingers and a sliding ring, provided according to the present invention, showing different positions of the sliding ring.
Figure 9B:
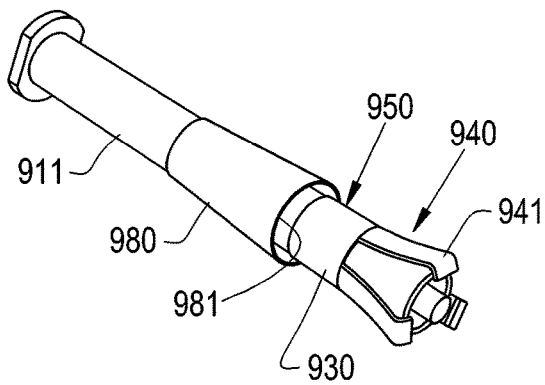
Figure 9C:
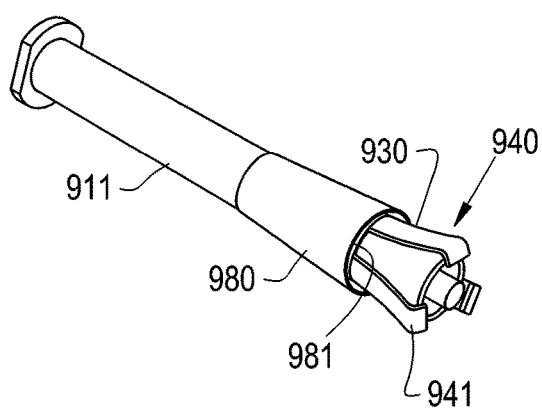
Figure 9D:
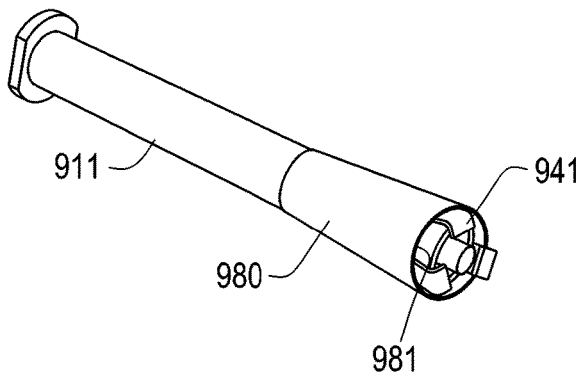

FIGS. 9A, 9B, 9C and 9D show perspective views of a detail of an exemplary embodiment of an apparatus for injecting a fluid, similar to the embodiment of FIG. 4. A needle retention device 930 includes a needle-retainer portion 940 with three elongated fingers 941 and a sliding ring 980 with an opening 981. In FIG. 9A, the needle retention device 930 is shown without the sliding ring 980. FIGS. 9B, 9C and 9D illustrate the sliding ring 980 in different positions.

As shown in FIG. 9A, the needle retention device 930 includes a container-contact portion 950, having a first opening that encloses a peripheral section of the container 911. In this manner, it can be, for example, easily attached to the container 911 by axial sliding onto the container 911. Further protrusions and/or recesses can be provided in order to form a firm connection between the needle retention device 930 and the container 911 with form-fitting. This connection can be secured, for example, by the sliding ring 980, when the sliding ring 980 is in the second axial position for locking the fingers 941. FIG. 9D shows the sliding ring 980 in this second axial position for locking the fingers 941.

Alternatively or additionally, the sliding ring 980 can press the container-contact portion 950 of the needle retention device 930 to the container 911 in order to establish a friction fit between the needle retention device 930 and the container 911 when the sliding ring 980 is in the second axial position for locking the fingers 941. The inner surface of the first opening of the container-contact portion 950 may include, at least in sections, a rough portion to increase the friction.

In addition, adhesives may be used to fix the needle retention device 930 and the container 911. But, these adhesives have to be selected such that they are suitable for use in the pharmaceutical field. Also, the use of adhesives is not sufficient for handling the needle with the needle retention device 30, for example after usage of the needle.

Figure 10:
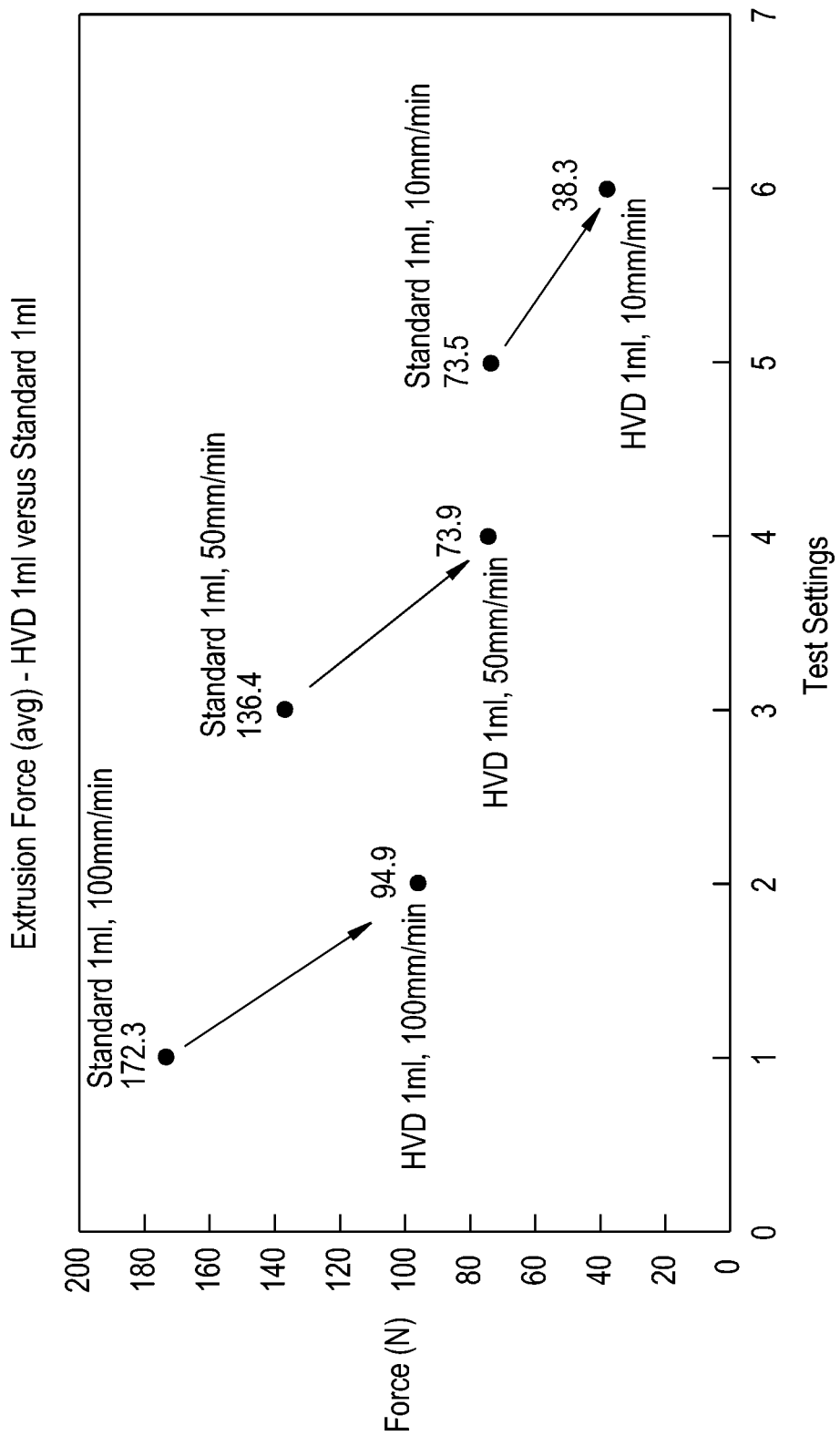
FIG. 10 is a diagram showing extrusion forces during tests.

FIG. 10 illustrates the extrusion force measured during tests with high viscous fluids. A small needle of 31 G was used. Very high applied forces have been observed which could lead to a needle pop off if the assembly of the needle and the syringe is not safe. A low assembly torque and/or contamination of the thread and/or the use of small needles may aggravate this problem. When no needle retention device is used, there is no visible evidence that the needle assembly is safe before the application of the fluid, in particular under high forces.

Figure 11:
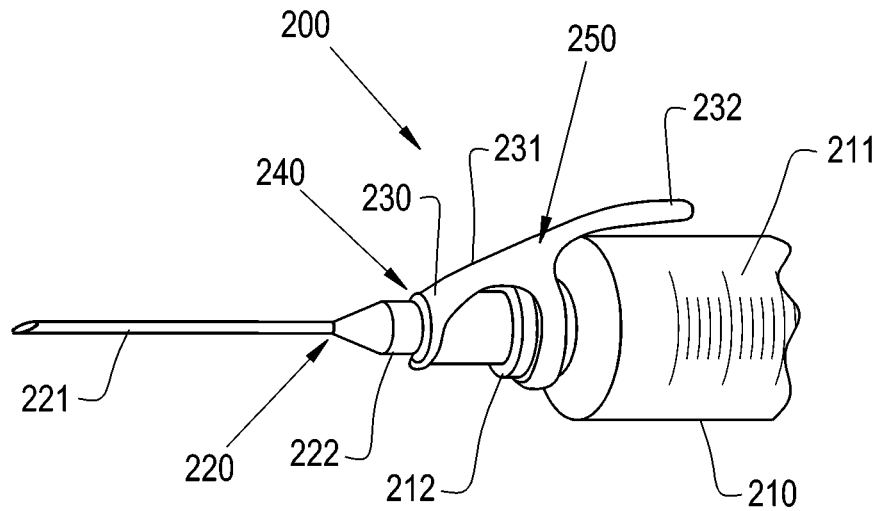
FIG. 11 is a perspective view of a detail of an exemplary embodiment of an apparatus for injecting a fluid, including an injector for injecting a fluid, a needle and a needle retention device, according to the embodiment of FIG. 2.

FIG. 11 shows a perspective view of a detail of an exemplary embodiment of an apparatus 200 for injecting a fluid including an injector 210 for injecting a fluid, a needle assembly 220 with a needle 221 and a hub 222, and a needle retention device 230, provided according to the embodiment of FIG. 2.

The needle retention device 230 of this embodiment can be made very cost effectively since it can be produced as a single piece accessory. The needle retention device 230 includes an extended elongated portion 232 that is constructed as a grip for easy handling. The grip enables a handling or a detachment of the needle assembly 220 without touching the needle 221, for example after usage of the needle.

The needle-retainer portion 240 includes two fingers, allowing a fixation around the hub. The container-contact portion 250 additionally includes a first opening to be engaged with a groove on the injector 210.

FIGS. 12A, 12B, 12C, and 12D are different views of a detail of an apparatus, showing the functionality of a locking ring 1270 and a sliding ring 1280. One objective of the present invention is to avoid any modifications of the container 1211 of the injector. In order to avoid these modifications, the present invention provides also a squeezing mechanism. In addition or alternatively, the fingers 1241 can be glued to the container 1211. But, as mentioned above, using adhesives causes some disadvantages that have to be taken into account.

The general principle of the locking ring 1270 and the sliding ring 1280 is shown in FIGS. 12A, 12B, 12C, and 12D. The locking ring 1270 is used to lock the assembly together and the sliding ring 1280 is used to close and open the fingers 1241 by sliding motion and rotation to lock the fingers 1241 in opened and closed positions.

Figure 13:
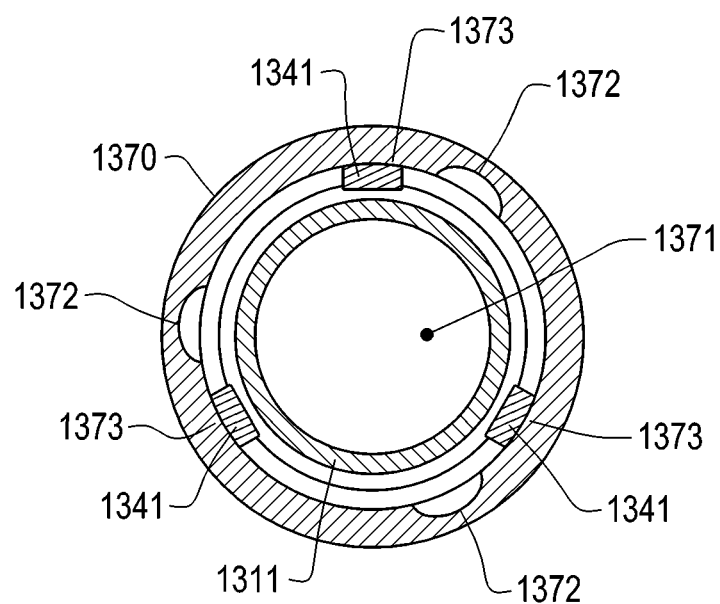
FIG. 13 is another view of the front side of the locking ring.
Figure 12A:
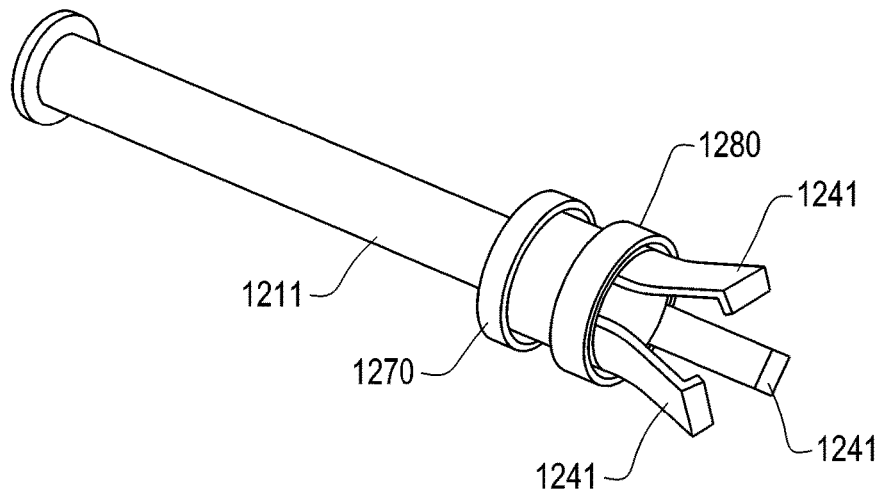
FIGS. 12A, 12B, 12C, and 12D are different views of a detail of an apparatus, showing the functionality of the locking ring.
Figure 12B:
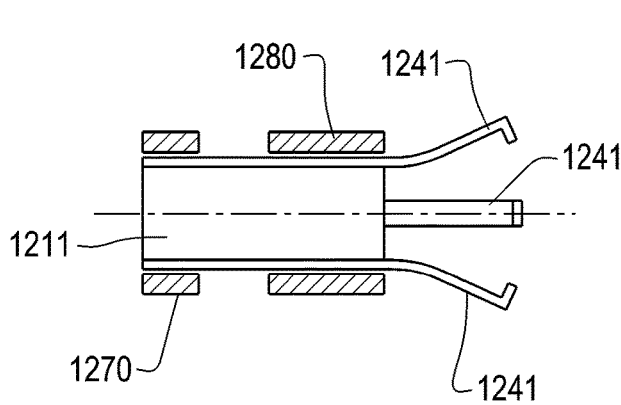
Figure 12C:
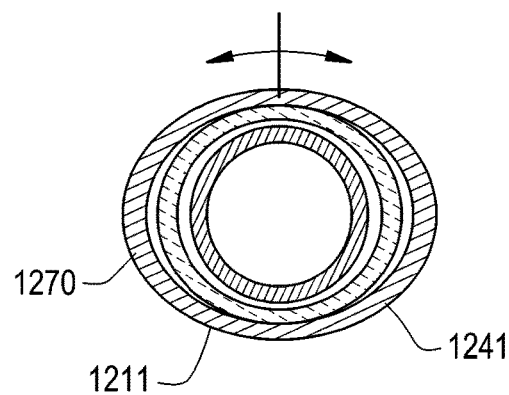
Figure 12D:
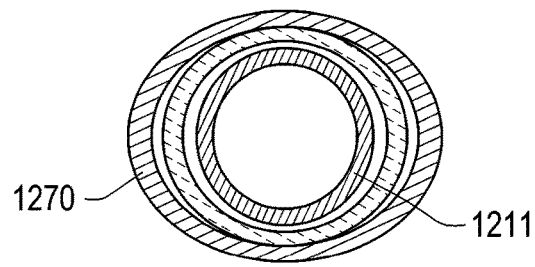

FIG. 13 shows another view of the front side of a container 1311 and a locking ring 1370. In this embodiment, the locking ring 1370 is arranged such that it can lock three fingers 1341.

For locking and unlocking the three fingers 1341, three recesses 1372 for unlocking and three protrusions 1373 for locking the fingers are provided at the inner surface of the opening 1371. The opening and closing of the fingers 1341 can be achieved through rotation of the locking ring 1370 as the legs enter the recesses 1372 within the locking ring 1370.

In an additional exemplary embodiment provided according to the present invention, the locking ring and/or the sliding ring and/or the needle retention device can be made, at least in sections, of a transparent material. This allows a user to see the locking status of the apparatus.

Figure 14:
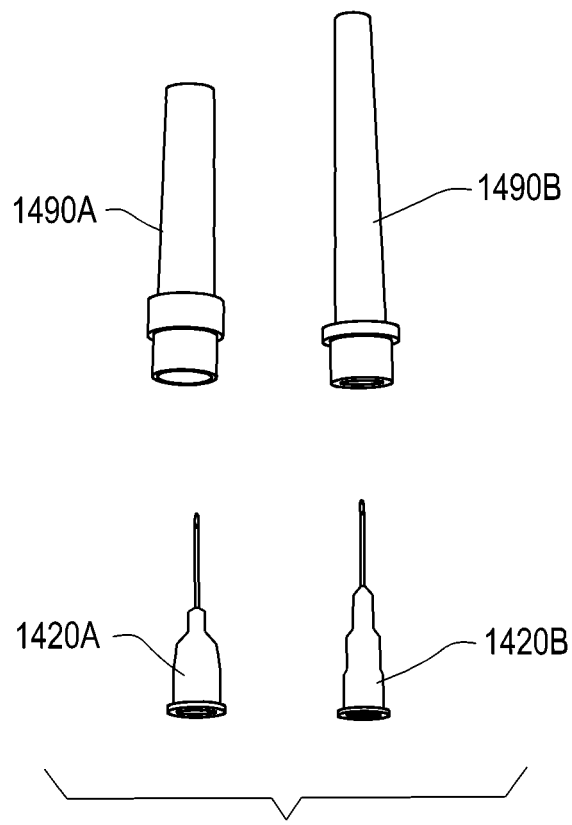
FIG. 14 is a plan view of two caps and two needle assemblies.

FIG. 14 shows, in a plan view, two different types of caps 1490A, 1490B and two different types of needle assemblies 1420A, 1420B. Normally, the caps 1490A, 1490B can be used for secure handling when mounting the needle assembly 1420A, 1420B to the injector. Before application of a fluid, the cap 1490A, 1490B can be removed and the needle retention device can be assembled to the injector.

Figure 15:
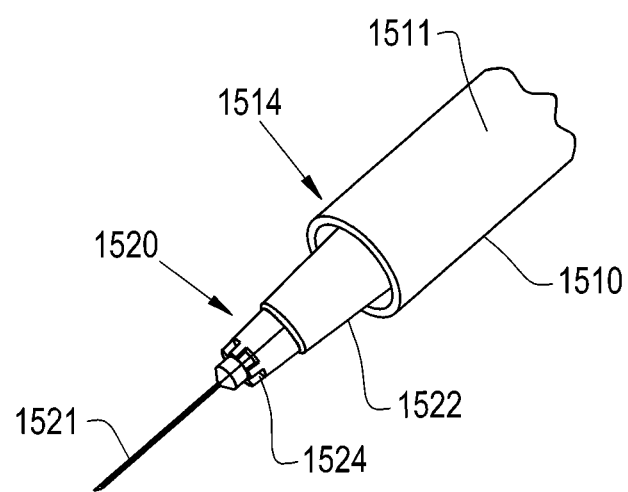
FIG. 15 is a perspective view of an exemplary embodiment of a needle assembly mounted to a syringe, provided according to the present invention.

FIG. 15 illustrates a needle assembly 1520 mounted to a syringe. The connection is made by a Luer lock connection, including a Luer lock connector 1514. The hub 1522 of the needle assembly 1520 is made with notches 1524, defining a shoulder. This shoulder enables the fingers to snap in or to engage with when in a locking position and, therefore, prevents the detachment of the needle assembly 1520, including a needle 1521, from the injector 1510, in particular when injecting a fluid from a container 1511.

Figure 16A:
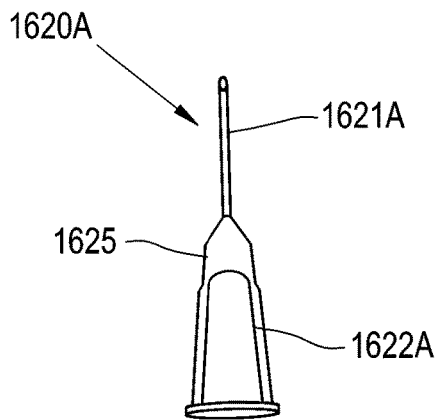
FIGS. 16A, 16B and 16C are plan views of different types of needle assemblies sufficient for use according to the present invention.
Figure 16B:
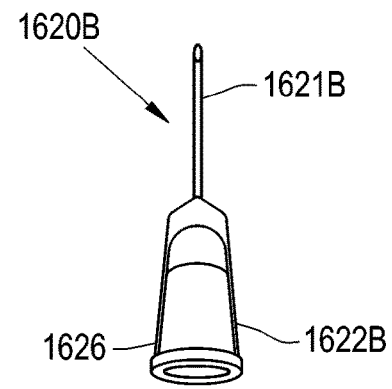
Figure 16C:
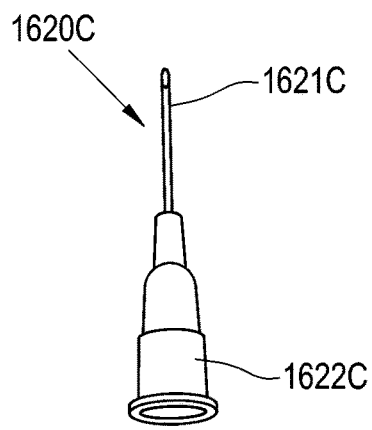

FIGS. 16A, 16B, and 16C show plan views of different types of needle assemblies 1620A, 1620B, 1620C sufficient for use according to the present invention. FIG. 16A shows a needle assembly 1620A having a needle 1621A of the size 30 G×½ Zoll that can be bought from the company Merz Pharma. This needle assembly 1620A includes a hub 1622A and fixation fins 1625.

FIG. 16B shows a needle assembly 1620B having a 30 G×½ Zoll needle 1621B, a hub 1622B, and a Luer lock connector 1626. FIG. 16C shows just another needle assembly 1620C with a needle 1621C and hub 1622C that can be bought from the company Terumo.

Figure 17:
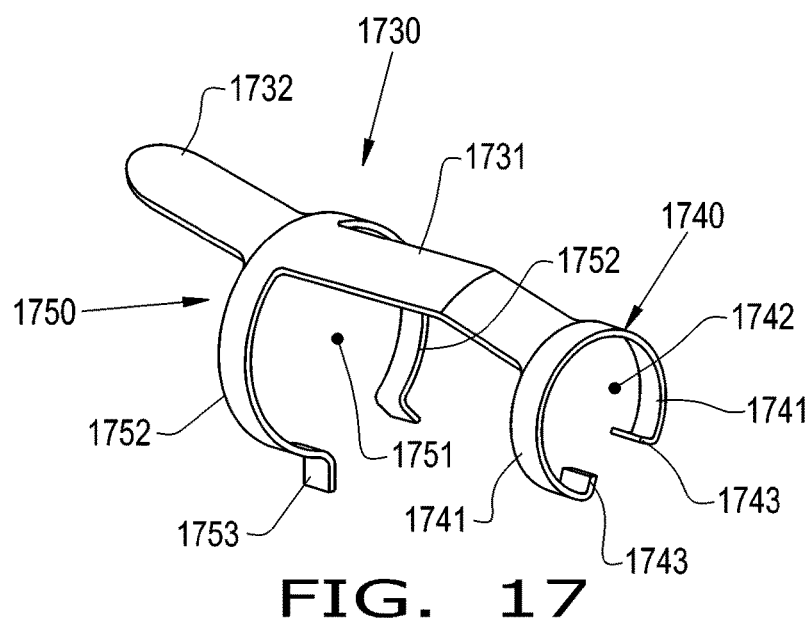
FIG. 17 is a perspective view of an exemplary embodiment of a needle retention device.

FIG. 17 shows a perspective view of an exemplary embodiment of a needle retention device 1730 with elongated portions 1731, 1732, including a needle-retainer portion 1740 with two fingers 1741, each including a hook 1743 to engage with a hub of a needle assembly and defining an opening 1742. The container-contact portion 1750 of this embodiment of the needle retention device 1730 also includes two contact fingers 1752, defining a first opening 1751, and arranged to encompass a peripheral section of an injector. The end portions 1753 of the contact fingers 1752 are widened to allow an easy and quick assembly onto the container.

Figure 18:
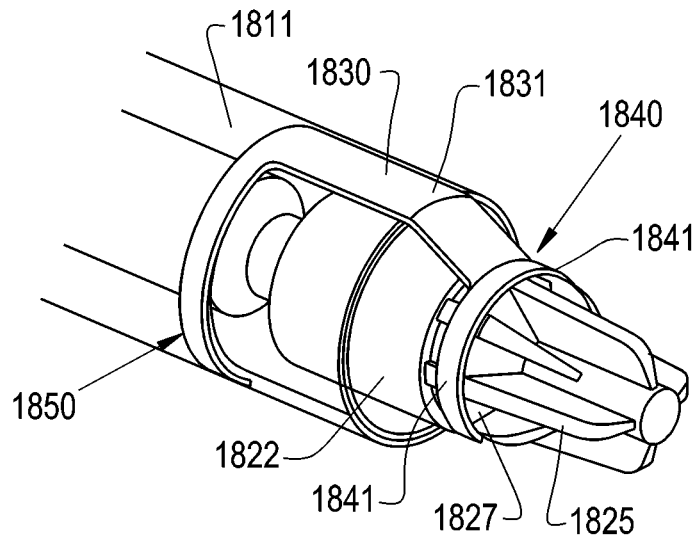
FIG. 18 is a perspective view of a detail of an exemplary embodiment of an apparatus for injecting a fluid, including an injector for injecting a fluid, a hub of a needle assembly, and a needle retention device.

FIG. 18 shows a perspective view of a detail of an exemplary embodiment of an apparatus for injecting a fluid including an injector with a container 1811 for injecting a fluid, a hub 1822 of a needle assembly, and a needle retention device 1830 with an elongated portion 1831 and a container-contact portion 1850.

In this embodiment, the hub 1822 includes fins 1825 defining a shoulder 1827 that allows a hook of a finger 1841 of a needle-retainer portion 1840 to snap in for establishing a form fit connection.

It can be understood and seen from the figures that such an assembly of a needle assembly and an injector is safe since the needle assembly can be screwed within the Luer lock. The needle assembly can be removed by screwing out the needle assembly. The needle retention device 1830 enables an operator to hold the hub 1822 without sticking himself with the needle.

Figure 19:
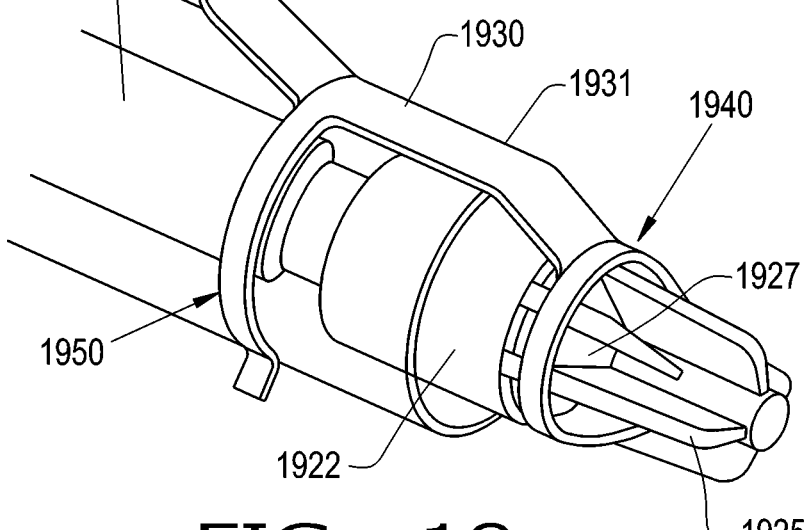
FIG. 19 is another perspective view of a detail of an exemplary embodiment of an apparatus for injecting a fluid, including an injector for injecting a fluid, a hub of a needle assembly, and a needle retention device.

FIG. 19 shows another perspective view of a detail of an exemplary embodiment of an apparatus for injecting a fluid including an injector with a container 1911 for injecting a fluid, a hub 1922 of a needle assembly, which may include fins 1925, and a needle retention device 1930 with elongated portions 1931, 1932, a needle-retainer portion 1940, and a container-contact portion 1950.

It can be seen from FIG. 19 that the fingers are placed within the notches or shoulder 1927 of the hub 1922. A rotation of the needle retention device 1930 and of the fingers in an axial movement will unscrew the hub 1922 out of Luer lock connector, and the needle (not shown in this view) can be disposed in a box for used needles, for example, without any close contact of the needle with the hand of the operator. Thus, this decreases the risk of being stuck for an operator when detaching a (used) needle. After disposing a used needle, for example, a new needle can be easily mounted within the Luer lock, at the same time the needle is protected within the cap during the screwing of the needle as shown in FIG. 14.

Figure 20:
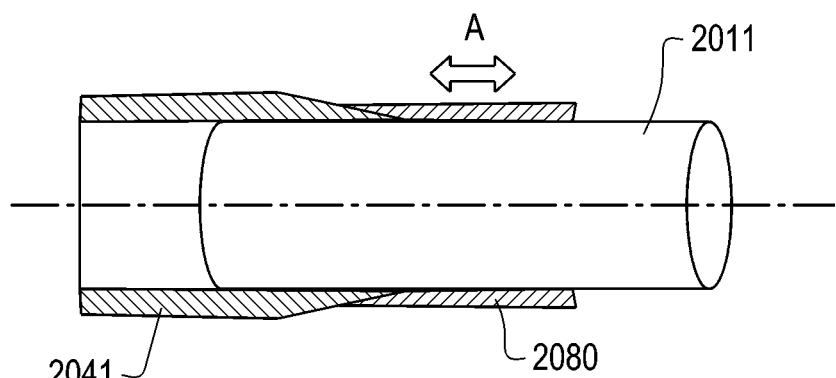
FIG. 20 is an illustration of the sliding mechanism of the sliding ring.

Finally, FIG. 20 shows an illustration of the sliding mechanism of a sliding ring 2080 along a container 2011 and/or a finger 2041. The sliding ring 2080 is designed for axial movement in two opposite axial directions as indicated by the arrow A.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

LIST OF REFERENCE SIGNS

100 Apparatus
110 Injector
111 Container
113 Peripheral Section
120 Needle Assembly
121 Needle
122 Hub
123 Contact Area
130 Needle Retention Device
131 Elongated Portion
140 Needle-Retainer Portion
141 Finger
142 Second Opening
150 Container-Contact Portion
151 First Opening
200 Apparatus
210 Injector
211 Container
212 Coupling Portion
220 Needle Assembly
221 Needle
222 Hub
230 Needle Retention Device
231 Elongated Portion
232 Extended Elongated Portion
240 Needle-Retainer Portion
250 Container-Contact Portion
290 Cap
300 Apparatus
310 Injector
311 Container
312 Coupling Portion
313 Peripheral Section
330 Needle Retention Device
333 Bumps
340 Needle-Retainer Portion
341 Finger
343 Hook
400 Apparatus
410 Injector
411 Container
412 Coupling Portion
413 Peripheral Section
430 Needle Retention Device
440 Needle-Retainer Portion
441 Finger
443 Hook
480 Sliding Ring
481 Opening of Sliding Ring
500 Apparatus
510 Injector
511 Container
513 Peripheral Section
520 Needle Assembly
521 Needle
522 Hub
523 Contact Area
530 Needle Retention Device
540 Needle-Retainer Portion
541 Finger
580 Sliding Ring
581 Opening of Sliding Ring
600 Apparatus
610 Injector
611 Container
613 Peripheral Section
620 Needle Assembly
621 Needle
622 Hub
623 Contact Area
630 Needle Retention Device
640 Needle-Retainer Portion
641 Finger
680 Sliding Ring
681 Opening of Sliding Ring
811 Container
841 Finger
870 Locking Ring
871 Opening of Locking Ring
872 Recess
873 Protrusion
911 Container
930 Needle Retention Device
940 Needle-Retainer Portion
941 Finger
950 Container-Contact Portion
980 Sliding Ring
981 Opening of Sliding Ring
1211 Container 1241 Finger
1270 Locking Ring
1280 Sliding Ring
1311 Container
1341 Finger
1370 Locking Ring
1371 Opening of Locking Ring
1372 Recess
1373 Protrusion
1420A Needle Assembly
1420B Needle Assembly
1490A Cap
1490B Cap
1510 Injector
1511 Container
1514 Luer Lock Connector (female)
1520 Needle Assembly
1521 Needle
1522 Hub
1524 Notch
1620A Needle Assembly
1620B Needle Assembly
1620C Needle Assembly
1621A Needle
1621B Needle
1621C Needle
1622A Hub
1622B Hub
1622C Hub
1625 Fins
1626 Luer Lock Connector (male)
1730 Needle Retention Device
1731 Elongated Portion
1732 Extended Elongated Portion
1740 Needle-Retainer Portion
1741 Finger
1742 Opening
1743 Hook
1750 Container-Contact Portion
1751 Opening
1752 Contact Finger
1753 End Portion
1811 Container
1822 Hub
1825 Fins
1827 Shoulder
1830 Needle Retention Device
1831 Elongated Portion
1840 Needle-Retainer Portion
1841 Finger
1850 Container-Contact Portion
1911 Container
1922 Hub
1925 Fins
1927 Shoulder
1930 Needle Retention Device
1931 Elongated Portion
1932 Extended Elongated Portion
1940 Needle-Retainer Portion
1950 Container-Contact Portion
2011 Container
2041 Finger
2080 Sliding Ring

What is claimed is:

1. An apparatus for injecting fluid, comprising:
an injector configured to inject a fluid, the injector comprising a cylindrical container configured for receiving and containing the fluid, a coupling portion, and a peripheral section;
a needle assembly comprising a needle and a hub, the hub defining a contact area, the coupling portion being configured to be coupled with the hub; and
a needle retention device comprising a needle-retainer portion having a plurality of fingers configured to radially extend over at least a part of the contact area of the hub, a container-contact portion defining a first opening configured to be attached in a form-fitting way onto the peripheral section of the container, wherein, when the apparatus is in its operational state for injecting the fluid, the hub of the needle assembly is coupled to the coupling portion of the container, the container-contact portion is attached to the container, and the plurality of fingers of the needle-retainer portion extends over at least a part of the contact area of the hub when the needle retention device is in its retaining position, the plurality of fingers comprising at least one first finger defining the first opening extending in a first plane and at least one second finger defining a second opening configured for circumferentially engaging a shoulder of the hub and extending in a second plane, the second plane being parallel with the first plane, wherein the needle retention device has a U-shape between the at least one first finger and the at least one second finger.

2. The apparatus of claim 1 wherein the needle retention device comprises a thermosetting material or a thermoplastic material adapted to pharmaceutical applications.

3. The apparatus of claim 1, wherein a color of the needle retention device is, at least partially, a signal color.

4. The apparatus of claim 3, wherein the color of the needle retention device is different from a color of at least one of the container, the needle, or the hub.

5. The apparatus of claim 1, wherein the second opening defines an inner diameter smaller than an outer diameter of the shoulder such that the fingers snap onto the shoulder to form a snap fit in a radial direction when mounted.

6. The apparatus of claim 1, wherein the first opening of the container-contact portion completely encloses the peripheral section of the container.

7. The apparatus of claim 1, wherein the coupling portion and the hub each include a Luer lock connector, and wherein the hub and the coupling portion are connected via the respective Luer lock connectors.

8. The apparatus of claim 1, wherein the needle retention device further includes an additional elongated portion extending parallel to a longitudinal axis of the container and defining a finger grip, the additional elongated portion configured for detaching the needle retention device.

9. The apparatus of claim 1, wherein the plurality of fingers are arranged parallel to each other and spaced apart from each other.

10. The apparatus of claim 9, wherein the fingers define equal distances to each other.

11. The apparatus of claim 1, wherein the needle retention device further includes a locking ring defining an opening configured for circumferentially enclosing the container-coupling portion, wherein the locking ring is configured for rotating around an axis of the container when mounted and has a recess for receiving the at least one finger when in a first, opened position when the at least one finger does not extend over a shoulder of the hub and pressing the at least one finger onto the shoulder when in a second, closed position.

12. The apparatus of claim 1, wherein the needle retention device further includes a sliding ring defining an opening configured for circumferentially enclosing the container-coupling portion, wherein the sliding ring is configured for axial movement along an axis of the container when mounted, releasing the at least one finger when in a first axial position and pressing the at least one finger into a shoulder of the hub when in a second axial position.

13. The apparatus of claim 1, wherein the needle is a small-bore needle having a size of an inner channel of less than or equal to that of a 30 Gauge needle, a 31 Gauge needle, a 32 Gauge needle, a 33 Gauge needle or a 34 Gauge needle.

14. The apparatus of claim 1, wherein the container is at least partially filled with the fluid.

15. The apparatus of claim 14, wherein the fluid has a viscosity in a range of at least 1 mPa*s.

16. The apparatus of claim 14, wherein the needle retention device prevents a detachment of the needle assembly from the injector when injecting the fluid, wherein a maximum force that can be applied to the fluid is at least 50 N.

17. The apparatus of claim 1, wherein the plurality of fingers extending over at least the part of the contact area of the hub, when the needle retention device is in its retaining position, prevents a detachment of the needle assembly from the container.

18. A needle retention device for an injection apparatus, comprising:

a needle-retainer portion including a plurality of fingers configured to radially extend over at least a part of a contact area of a hub of a needle assembly and a container-contact portion defining a first opening configured to be attached in a form-fitting way onto a peripheral section of a container of an injector of the apparatus, the plurality of fingers being movable from a first position to a second position, the plurality of fingers being configured to lock the hub in the second position and unlock the hub in the first position, the plurality of fingers comprising at least one first finger defining the first opening extending in a first plane and at least one second finger defining a second opening configured for circumferentially engaging a shoulder of the hub and extending in a second plane, the second plane being parallel with the first plane, wherein the needle retention device has a U-shape between the at least one first finger and the at least one second finger.

19. The needle retention device of claim 18, wherein the plurality of fingers moves radially outward from the second position to the first position.

20. The needle retention device of claim 18, further comprising a locking ring associated with the at least one finger, the locking ring being movable from an opened position that allows movement of the at least one finger between the second position and the first position and a closed position that prevents movement of the at least one finger between the second position and the first position.

* * * * *